(12) United States Patent
Gerber et al.

US008377933B2

(10) Patent No.: US 8,377,933 B2
(45) Date of Patent: Feb. 19, 2013

(54) METHOD FOR TREATING A PULMONARY HYPERTENSION CONDITION

(75) Inventors: Michael J. Gerber, Denver, CO (US); Christopher Dufton, Nederland, CO (US)

(73) Assignee: Gilead Colorado, Inc., Westminster, CO (US)

( * ) Notice: Subject to any disclaimer, the term of this patent is extended or adjusted under 35 U.S.C. 154(b) by 0 days.

(21) Appl. No.: 13/162,137

(22) Filed: Jun. 16, 2011

(65) Prior Publication Data

US 2011/0245253 A1    Oct. 6, 2011

Related U.S. Application Data

(63) Continuation of application No. 12/706,818, filed on Feb. 17, 2010, now abandoned, which is a continuation of application No. 11/953,955, filed on Dec. 11, 2007, now abandoned.

(60) Provisional application No. 60/869,667, filed on Dec. 12, 2006.

(51) Int. Cl.
*A61K 31/53*    (2006.01)
(52) U.S. Cl. ............... 514/243; 514/274; 514/250
(58) Field of Classification Search ............. 514/243, 514/274, 250
See application file for complete search history.

(56) References Cited

U.S. PATENT DOCUMENTS

| 7,902,195 B2 * | 3/2011 | Hughes et al. | 514/249 |
| 2008/0139593 A1 | 6/2008 | Gerber et al. | 514/274 |
| 2010/0152217 A1 | 6/2010 | Gerber et al. | 514/274 |

FOREIGN PATENT DOCUMENTS

| WO | WO 2006/007213 | 1/2006 |
| WO | WO 2010/062640 | 6/2010 |

OTHER PUBLICATIONS

Marius Hoeper, Drugs, 2005,65(10):1337-1354.*
Beghetti, D.J. (2006) "Current treatment options in children with pulmonary arterial hypertension and experiences with oral bosentan." Eur. J. Clinical Investigation, 36(Suppl. 3):16-24.
Galié, et al. (2005) "Ambrisentan therapy for pulmonary arterial hypertension." J. Am. Coll. Cardiol. 46(3):529-535.
Levine, D.J. (2006) "Diagnosis and management of pulmonary arterial hypertension: Implications for respiratory care." Respiratory Care 51(4): 368-381.
Mohan (2005) "Importance of screening and early detection of pulmonary hypertension and current treatment options." J. Postgrad. Med. 51(2):107.
Myogen Inc.: "Ambrisentan phase II results presented at ATS 2004" PRNEWSWIRE.COM, [online] Jan. 27, 2005: http://www.prnewswire.com/cgi-bin/stories.pl?ACCT=104&STORY=/www/story/05-24-2004/0002180826&EDATE=>.

Myogen, Inc. News Release, Dec. 4, 2003 (http://www.prnewswire.com/cgi-bin/stories.pl?ACCT=104&STORY=/www/story/12-04-2003/0002069898&EDATE).
Myogen, Inc. News Release, Jan. 8, 2004 (http://investor.myogen.com/phoenix.zhtml?c=135160&p=irol-newsArticle&ID=759080&highlight).
Myogen, Inc. News Release, Feb. 16, 2004 (http://investor.myogen.com/phoenix.zhtml?c=135160&p=irol-newsArticle&ID=759478&highlight).
Myogen, Inc. News Release, May 24, 2004 (http://investor.myogen.com/phoenix.zhtml?c=135160&p=irol-newsArticle&ID=759469&highlight).
Myogen, Inc. News Release, Feb. 10, 2005 (http://investor.myogen.com/phoenix.zhtml?c=135160&p=irol-newsArticle&ID=759971&highlight).
Myogen, Inc. News Release, May 19, 2005 (http://investor.myogen.com/phoenix.zhtml?c=135160&p=irol-newsArticle&ID=759658&highlight).
Myogen, Inc. News Release, May 23, 2005 (http://investor.myogen.com/phoenix.zhtml?c=135160&p=irol-newsArticle&ID=759656&highlight).
Myogen, Inc. News Release, Jul. 21, 2005 (http://investor.myogen.com/phoenix.zhtml?c=135160&p=irol-newsArticle&ID=759650&highlight).
Myogen, Inc. News Release, Nov. 10, 2005 (http://investor.myogen.com/phoenix.zhtml?c=135160&p=irol-newsArticle&ID=781654&highlight).
Myogen, Inc. News Release, Dec. 12, 2005 (http://investor.myogen.com/phoenix.zhtml?c=135160&p=irol-newsArticle&ID=794738&highlight).
Myogen, Inc. News Release, Feb. 13, 2006 (http://investor.myogen.com/phoenix.zhtml?c=135160&p=irol-newsArticle&ID=815989&highlight).
Myogen, Inc. News Release, Mar. 2, 2006 (http://investor.myogen.com/phoenix.zhtml?c=135160&p=irol-newsArticle&ID=824548&highlight).
Myogen, Inc. News Release, Apr. 10, 2006 (http://investor.myogen.com/phoenix.zhtml?c=135160&p=irol-newsArticle&ID=840536&highlight).
Myogen, Inc. News Release, May 3, 2006 (http://investor.myogen.com/phoenix.zhtml?c=135160&p=irol-newsArticle&ID=851641&highlight).
Myogen, Inc. News Release, May 8, 2006 (http://investor.myogen.com/phoenix.zhtml?c=135160&p=irol-newsArticle&ID=853198&highlight).
Myogen, Inc. News Release, May 24, 2006 (http://investor.myogen.com/phoenix.zhtml?c=135160&p=irol-newsArticle&ID=860158&highlight).
Myogen Jun. 2006 presentation available at library.corporate-ir.net/library/13/135/135160/items/203236/Junepresentation.pdf.

(Continued)

*Primary Examiner* — Rei-tsang Shiao
(74) *Attorney, Agent, or Firm* — Harness, Dickey & Pierce, P.L.C.; J. Timothy Keane; Kisuk Lee

(57) ABSTRACT

A method for treating a pulmonary hypertension condition such as pulmonary arterial hypertension (PAH) in a subject comprises administering to the subject a therapeutically effective amount of ambrisentan, wherein, at baseline, time from first diagnosis of the condition in the subject is not greater than about 2 years.

11 Claims, 2 Drawing Sheets

OTHER PUBLICATIONS

Myogen, Inc. News Release, Aug. 7, 2006 (http://investor.myogen.com/phoenix.zhtml?c=135160&p=irol-newsArticle&ID=892987&highlight).

Myogen, Inc. News Release, Sep. 5, 2006 (http://investor.myogen.com/phoenix.zhtml?c=135160&p=irol-newsArticle&ID=902050&highlight).

Myogen, Inc. News Release, Oct. 10, 2006 (http://investor.myogen.com/phoenix.zhtml?c=135160&p=irol-newsArticle&ID=913787&highlight).

Rubin (2004) "Introduction: Diagnosis and management of pulmonary arterial hypertension: ACCP evidence-based clinical practice guidelines." Chest 126:7-10.

Rubin, et al.(2005) "Ambrisentan for pulmonary arterial hypertension." Future Cardiol. 1(4):1-8.

International Search Report (ISR) and Written Opinion (WO) in PCT/US2007/087058 dated Apr. 12, 2008, which is the international counterpart to the present application.

* cited by examiner

METHOD FOR TREATING A PULMONARY HYPERTENSION CONDITION

CROSS REFERENCE TO RELATED APPLICATIONS

This application is a continuation of U.S. application Ser. No. 12/706,818, filed Feb. 17, 2010 which is a continuation of U.S. application Ser No. 11/953,955, filed Dec. 11, 2007 which claims the benefit of U.S. provisional application Ser. No. 60/869,667, filed Dec. 12, 2006, incorporated in their entirety herein by reference.

FIELD OF THE INVENTION

The present invention relates to methods useful for treating a subject having a pulmonary hypertension condition, and for improving clinical outcome in such a subject.

BACKGROUND OF THE INVENTION

Pulmonary hypertension (PH) has been previously classified as primary (idiopathic) or secondary. Recently, the World Health Organization (WHO) has classified pulmonary hypertension into five groups:

Group 1: pulmonary arterial hypertension (PAH);
Group 2: PH with left heart disease;
Group 3: PH with lung disease and/or hypoxemia;
Group 4: PH due to chronic thrombotic and/or embolic disease; and
Group 5: miscellaneous conditions (e.g., sarcoidosis, histiocytosis X, lymphangiomatosis and compression of pulmonary vessels).

See, for example, Rubin (2004) *Chest* 126:7-10.

Pulmonary arterial hypertension (PAH) is a serious, progressive and life-threatening disease of the pulmonary vasculature, characterized by profound vasoconstriction and an abnormal proliferation of smooth muscle cells in the walls of the pulmonary arteries. Severe constriction of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in pulmonary vascular resistance (PVR) and sustained elevations in pulmonary artery pressure (PAP), which ultimately lead to right ventricular failure and death. Patients diagnosed with PAH have a poor prognosis and equally compromised quality of life, with a mean life expectancy of 2 to 5 years from the time of diagnosis if untreated.

Endothelin-1 (ET-1) is the primary member of a family of potent vasoconstrictor peptides, which are known to play an essential role in mammalian cardiovascular physiology. ET-1 is synthesized de novo and released from endothelial cells in response to a variety of factors, including angiotensin II, catecholamines, cytokines, hypoxia and shear stress. Two receptor subtypes, endothelin receptor type A ($ET_A$) and endothelin receptor type B ($ET_B$), mediate the effects of ET-1. In humans, the $ET_A$ receptor is preferentially expressed in vascular smooth muscle cells and is primarily responsible for the vasoconstrictive effects of ET-1. In contrast, $ET_B$ receptors are found mainly in the vascular endothelium, and their activation results in vasodilatation via production of nitric oxide and prostacyclin. The $ET_B$ receptor is also involved in regulation of circulating concentrations of ET-1, through effects on endothelin converting enzyme (ECE-1) expression, and the synthesis and reuptake of ET-1 by endothelial cells.

Ambrisentan is a non-sulfonamide, propanoic acid-class endothelin receptor antagonist (ERA) with high affinity (~12 µM) for the $ET_A$ receptor. Bosentan, a non-selective, sulfonamide-class ERA, is approved for treatment of PAH in patients with WHO functional class III or IV symptoms. Sitaxsentan is another sulfonamide-class ERA that is selective for the $ET_A$ receptor. Sitaxsentan is currently under review for market authorization as a PAH therapeutic.

Myogen, Inc. News Release, Dec. 4, 2003 (http://www.prnewswire.com/cgi-bin/stories.pl?ACCT=104&STORY=/www/story/12-04-2003/0002069898&EDATE=) announced completion of a Phase II trial of ambrisentan in PAH and initiation of Phase III trials. The release stated that the Phase III trials would evaluate 2.5 mg, 5.0 mg and 10.0 mg oral dosages of ambrisentan administered once a day, and would have as a primary efficacy endpoint exercise capacity, which measures the change from baseline in 6-minute walk distance (6MWD) compared to placebo, and secondary endpoints including Borg dyspnea index (BDI), WHO functional class and a quality of life assessment.

Myogen, Inc. News Release, Jan. 8, 2004 (http://investor.myogen.com/phoenix.zhtml?c=135160&p=irol-newsArticle&ID=759080&highlight=) announced patient enrollment in phase III clinical trials of ambrisentan for treatment of PAH. According to the news release, phase II trials had demonstrated a statistically significant and clinically meaningful increase in the primary efficacy endpoint (exercise capacity measured by 6MWD) in all four ambrisentan dose groups tested.

Myogen, Inc. News Release, Feb. 16, 2004 (http://investor.myogen.com/phoenix.zhtml?c=135160&p=irol-newsArticle&ID=759478&highlight=) announced upcoming presentation of detailed results of the phase II study of ambrisentan in PAH, at the American Thoracic Society (ATS) 2004 International Conference. (Rubin (2004) "Ambrisentan Improves Exercise Capacity and Clinical Measures in Pulmonary Arterial Hypertension", ATS May 21-26, 2004.)

Myogen, Inc. News Release, May 24, 2004 (http://investor.myogen.com/phoenix.zhtml?c=135160&p=irol-newsArticle&ID=759469&highlight=) reported improvements in 6MWD, BDI and WHO functional classification seen in the Phase II study. Additionally, the news release mentioned suitability of ambrisentan for once-a-day dosing.

Myogen, Inc. News Release, Feb. 10, 2005 (http://investor.myogen.com/phoenix.zhtml?c=135160&p=irol-newsArticle&ID=759971&highlight=) announced that two abstracts describing effects of ambrisentan in patients with PAH were selected for presentation at ATS 2005 in San Diego. (Galié (2005) "Ambrisentan Long-Term Safety and Efficacy in Pulmonary Arterial Hypertension 1-Year Follow-Up", ATS May 23, 2005; Frost (2005) "Ambrisentan Improves 6MWD Comparably for WHO Class II and III PAH Patients," ATS May 22, 2005.) It was stated that one-year data demonstrated that ambrisentan produced a significant and durable benefit on exercise capacity and other clinical measures of PAH and that WHO Class II and III PAH patients have significant and comparable improvement in exercise capacity, suggesting that the effects of ambrisentan are not limited by the "ceiling effect" in patients with less severe PAH symptoms.

Myogen, Inc. News Release, May 19, 2005 (http://investor.myogen.com/phoenix.zhtml?c=135160&p=irol-newsArticle&ID=759658&highlight=) reported initiation of a clinical trial to evaluate ambrisentan in patients with PAH who have previously discontinued bosentan or sitaxsentan therapy due to liver function test (LFT) abnormalities, specifically elevated serum aminotransferase concentrations.

Myogen, Inc. News Release, May 23, 2005 (http://investor.myogen.com/phoenix.zhtml?c=135160&p=irol-newsArticle&ID=759656&highlight=) reported further data presented by Galié (2005) ATS 2005, cited above, which were stated to show improvements in a 6-minute walking test (6MWT) accompanied with improved levels of dyspnea (breathlessness) for WHO Class II and III patients. The release reported a one-year survival rate of 92% for patients with idiopathic PAH as compared to an NIH registry predicted survival of 74%.

Myogen, Inc. News Release, Jul. 21, 2005 (http://investor.myogen.com/phoenix.zhtml?c=135160&p=irol-newsArticle&ID=759650&highlight=) announced completion of enrollment of 187 patients in ARIES-2, one of the two Phase III clinical trials of ambrisentan in patients with PAH. The news release reported that ARIES-1 evaluates doses of 5.0 mg and 10.0 mg of ambrisentan administered orally once daily, while ARIES-2 provides 2.5 mg and 5.0 mg dosages. The release stated that the results of the Phase II clinical trial of ambrisentan in patients with PAH demonstrated significant improvements in 6MWD, BDI and WHO functional class, durable efficacy with long-term use and a possible survival benefit, comparable efficacy in WHO Functional Class 2 and Class 3 patients, selectivity for the endothelin type-A receptor, dose flexibility, true once-daily dosing, no drug interactions (no p450 induction or inhibition), and low incidence and severity of potential liver toxicity that does not appear to be dose related.

Myogen, Inc. News Release, Nov. 10, 2005 (http://investor.myogen.com/phoenix.zhtml?c=135160&p=irol-newsArticle&ID=781654&highlight=) announced the expectation that ARIES-2 results would be reported in December of that year.

Rubin et al. (2005) *Future Cardiol.* 1(4):1-8 reported improvement of the mean 6MWD for all patients after 12 weeks of ambrisentan treatment, with a mean increase from baseline of 36 meters. The authors reported that similar improvements in 6MWD were observed for patients with WHO Functional Class II and III symptoms, indicating that the effects of ambrisentan may not be limited by a "ceiling effect" in less advanced PAH patients, as has been reported for sitaxsentan. Additionally, the authors reported that clinically meaningful improvements were also seen in BDI and WHO functional class.

Galié et al. (2005) *J. Am. Coll. Cardiol.* 46(3):529-535 reported results of a randomized dose-ranging study examining efficacy and safety of ambrisentan in patients with PAH. The authors reported an increase in exercise capacity in patients with idiopathic PAH as well as in patients with PAH due to other etiologies and for patients in WHO Functional Class II as well as those in WHO Functional Class III.

PAH afflicts approximately 200,000 patients worldwide. Improved drug therapies to treat pulmonary hypertensive disorders such as PAH are needed in the art. Further, methods for enhancing the clinical outcome for patients having pulmonary hypertension conditions would be highly desirable.

SUMMARY OF THE INVENTION

There is now provided a method for treating a pulmonary hypertension condition in a subject, comprising administering a therapeutically effective amount of ambrisentan to the subject, wherein, at baseline, time from first diagnosis of the condition in the subject is not greater than about 2 years.

There is further provided a method for providing an improved prognosis for a subject having a pulmonary hypertension condition, comprising administering to the subject ambrisentan at a dose and frequency and for a treatment period effective to provide (a) a reduction of at least about 25% in probability of a clinical worsening event during the treatment period, and/or (b) a reduction from baseline of at least about 15% in serum brain natriuretic peptide (BNP) concentration; wherein, at baseline, time from first diagnosis of the condition in the subject is not greater than about 2 years.

There is still further provided a method for prolonging life of a subject having a pulmonary hypertension condition, comprising administering to the subject ambrisentan at a dose and frequency and for a treatment period effective to increase life expectancy, from a time of initiation of treatment, by at least about 30 days; wherein, at baseline, time from first diagnosis of the condition in the subject is not greater than about 2 years.

There is still further provided a method for extending time to clinical worsening in a subject having PAH, comprising administering to the subject ambrisentan at a dose and frequency and for a treatment period effective to decrease the probability of a clinical worsening event by at least about 25%; wherein, at baseline, time from first diagnosis of the condition in the subject is not greater than about 2 years.

There is still further provided a method for treating a pulmonary hypertension condition in a reproductively active male subject, the method comprising administering a therapeutically effective amount of ambrisentan to the subject, wherein fertility of the subject is not substantially compromised.

Any of the above methods is applicable to any pulmonary hypertension condition recognized in the WHO classification, including pulmonary arterial hypertension (PAH) as classified in WHO Group 1.

There is still further provided a method for treating PAH in a subject, comprising administering a therapeutically effective amount of ambrisentan to the subject, wherein the PAH is associated with one or more of (a) a congenital heart defect such as a systemic-to-pulmonary shunt or Eisenmenger's syndrome, (b) portal hypertension, (c) use of a drug or toxin other than an anorexigen, (d) thyroid disorder, (e) glycogen storage disease, (f) Gaucher disease, (g) hereditary hemorrhagic telangiectasia, (h) hemoglobinopathy, (i) myeloproliferative disorder, (j) splenectomy, (k) pulmonary veno-occlusive disease and/or (l) pulmonary capillary hemangiomatosis.

There is still further provided a method for treating a pulmonary hypertension condition classified in WHO Groups 2-5 in a subject, comprising administering a therapeutically effective amount of ambrisentan to the subject.

Other embodiments, including particular aspects of the embodiments summarized above, will be evident from the detailed description that follows.

DETAILED DESCRIPTION

Figure 1:
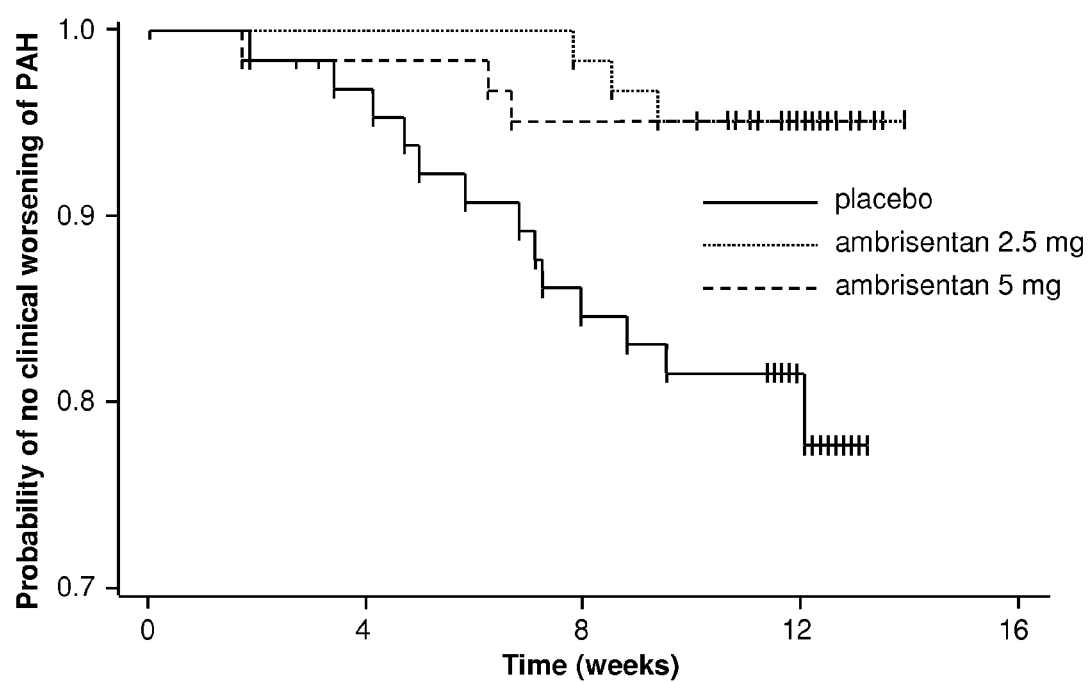
FIG. 1 provides Kaplan-Meier curves for time to clinical worsening of PAH from the study described in Example 1.

The present invention is based in part on a finding, in placebo-controlled clinical trials, that ambrisentan is effective for treatment of a pulmonary hypertension condition, more specifically pulmonary arterial hypertension (PAH), in subjects wherein the condition is relatively recently diagnosed. In the above-referenced presentation by Rubin (2004) at ATS 2004, subjects treated with ambrisentan were reportedly characterized at baseline by a mean time since diagnosis of 3.2±3.8 years. In the absence of placebo control, it is not possible to determine how these subjects might have fared had they not been given the benefit of ambrisentan therapy.

It is noted, however, that a prediction based on the National Institutes for Health (NIH) registry is that only 74% of patients having a diagnosis of idiopathic PAH survive for 1 year (above-referenced presentation by Galié (2005) at ATS 2005). A cohort of patients that have survived with the disease for a longer period of time may not be representative of patients with more recent diagnosis, as that cohort may be inadvertently biased in favor of individuals better able to survive for a prolonged period.

The sooner treatment can begin after diagnosis, the better. Accordingly, in a first embodiment of the invention, a method for treating a pulmonary hypertension condition in a subject comprises administering a therapeutically effective amount of ambrisentan to the subject, wherein, at baseline, time from first diagnosis of the condition in the subject is not greater than about 2 years, for example not greater than about 1.5 years, not greater than about 1 year, not greater than about 0.75 year or not greater than about 0.5 year. In one aspect of the first embodiment, administration of ambrisentan can begin substantially immediately, for example within about one month or within about one week, upon diagnosis.

This method does not in any way negate ambrisentan therapy for subjects having a longer history of the condition. However, it recognizes that early intervention is advantageous. Benefits of the method to subjects having recent diagnosis (and poor prognosis without early intervention as exhibited, for example, in the NIH registry mentioned above) have now been quantified for the first time. Illustratively, in the placebo-controlled study described in Example 1 below, the median number of years for which PAH was present at baseline was 0.38 for subjects receiving placebo, 0.43 years for subjects receiving 2.5 mg ambrisentan daily, and 0.26 years for subjects receiving 5 mg ambrisentan daily. In the placebo-controlled study described in Example 2 below, the median number of years for which PAH was present at baseline was 0.54 for subjects receiving placebo, 0.33 years for subjects receiving 5 mg ambrisentan daily, and 0.60 years for subjects receiving 10 mg ambrisentan daily.

Except where otherwise indicated herein, the term "baseline" herein means a time immediately prior to initiation of treatment with ambrisentan.

The term "diagnosis" herein means recognition by a physician or clinician of a pulmonary hypertension condition, for example PAH, in the subject, by any means whether or not such diagnosis is confirmed by hemodynamic evaluation. In one aspect of the first embodiment, diagnosis is confirmed hemodynamically, for example in the case of PAH by presence of one or more, more typically two or all three of the following:
  (a) mean pulmonary arterial pressure (PAP) not less than about 25 mmHg at rest or not less than about 30 mmHg while exercising;
  (b) pulmonary vascular resistance (PVR) not less than about 3 mmHg/liter/minute;
  (c) pulmonary capillary wedge pressure (PCWP) or left ventricle end diastolic pressure (LVEDP) not greater than about 15 mmHg.

The pulmonary hypertension condition diagnosed, and treated by the method of the first embodiment, can comprise any one or more of the conditions recognized according to the World Health Organization (WHO) or Venice (2003) classification (see, for example, Rubin (2004) *Chest* 126:7-10):
  Group 1: Pulmonary arterial hypertension (PAH)
    1.1 idiopathic PAH
    1.2 familial PAH
    1.3 PAH associated with:
      1.3.1 collagen vascular disease
      1.3.2 congenital systemic-to-pulmonary shunts (including Eisenmenger's syndrome)
      1.3.3 portal hypertension
      1.3.4 HIV infection
      1.3.5 drugs and toxins
      1.3.6 other (thyroid disorders, glycogen storage disease, Gaucher disease, hereditary hemorrhagic telangiectasia, hemoglobinopathies, myeloproliferative disorders, splenectomy)
    1.4 PAH associated with significant venous or capillary involvement
      1.4.1 pulmonary veno-occlusive disease (PVOD)
      1.4.2 pulmonary capillary hemangiomatosis (PCH)
    1.5 persistent pulmonary hypertension of the newborn
  Group 2: Pulmonary hypertension with left heart disease
    2.1 left-sided atrial or ventricular heart disease
    2.2 left-sided valvular heart disease
  Group 3: Pulmonary hypertension associated with lung diseases and/or hypoxemia
    3.1 chronic obstructive pulmonary disease (COPD)
    3.2 interstitial lung disease
    3.3 sleep-disordered breathing
    3.4 alveolar hypoventilation disorders
    3.5 chronic exposure to high altitude
    3.6 developmental abnormalities
  Group 4: Pulmonary hypertension due to chronic thrombotic and/or embolic disease
    4.1 thromboembolic obstruction of proximal pulmonary arteries
    4.2 thromboembolic obstruction of distal pulmonary arteries
    4.3 non-thrombotic pulmonary embolism (tumor, parasites, foreign material)
  Group 5: Miscellaneous (sarcoidosis, histiocytosis X, lymphangiomatosis, compression of pulmonary vessels (adenopathy, tumor, fibrosing mediastinitis))

In one aspect, the pulmonary hypertension condition comprises PAH (WHO Group 1), for example idiopathic PAH, familial PAH or PAH associated with another disease or condition.

Pulmonary hypertension at baseline can be mild, moderate or severe, as measured for example by WHO functional class, which is a measure of disease severity in patients with pulmonary hypertension. The WHO functional classification is an adaptation of the New York Heart Association (NYHA) system and is routinely used to qualitatively assess activity tolerance, for example in monitoring disease progression and response to treatment (Rubin (2004) *Chest* 126:7-10). Four functional classes are recognized in the WHO system:
  Class I: pulmonary hypertension without resulting limitation of physical activity; ordinary physical activity does not cause undue dyspnea or fatigue, chest pain or near syncope;
  Class II: pulmonary hypertension resulting in slight limitation of physical activity; patient comfortable at rest; ordinary physical activity causes undue dyspnea or fatigue, chest pain or near syncope;
  Class III: pulmonary hypertension resulting in marked limitation of physical activity; patient comfortable at rest; less than ordinary activity causes undue dyspnea or fatigue, chest pain or near syncope;

Class IV: pulmonary hypertension resulting in inability to carry out any physical activity without symptoms; patient manifests signs of right-heart failure; dyspnea and/or fatigue may be present even at rest; discomfort is increased by any physical activity.

In one aspect of the first embodiment, the subject at baseline exhibits pulmonary hypertension (e.g., PAH) of at least WHO Class II, for example WHO Class II or Class III.

In another aspect, the subject at baseline exhibits mean PAP at rest of at least about 30 mmHg, for example at least about 35, at least about 40, at least about 45 or at least about 50 mmHg.

The term "treatment" herein encompasses one or more of the following:

(a) adjustment of one or more hemodynamic parameters towards a more normal level, for example lowering mean PAP or PVR, or raising PCWP or LVEDP, versus baseline;
(b) improvement of pulmonary function versus baseline, for example increasing exercise capacity, illustratively as measured in a test of 6-minute walking distance (6MWD), or lowering Borg dyspnea index (BDI);
(c) improvement of one or more quality of life parameters versus baseline, for example an increase in score on at least one of the SF-36® health survey functional scales;
(d) general improvement versus baseline in the severity of the condition, for example by movement to a lower WHO functional class;
(e) improvement of clinical outcome following a period of treatment, versus expectation in absence of treatment (e.g., in a clinical trial setting, as measured by comparison with placebo), including improved prognosis, extending time to or lowering probability of clinical worsening, extending quality of life (e.g., delaying progression to a higher WHO functional class or slowing decline in one or more quality of life parameters such as SF-36® health survey parameters), and/or increasing longevity; and/or
(f) adjustment towards a more normal level of one or more molecular markers that can be predictive of clinical outcome (e.g., plasma concentrations of endothelin-1 (ET-1), cardiac troponin T (cTnT) or B-type natriuretic peptide (BNP)).

Except where otherwise indicated herein, a "therapeutically effective amount" of ambrisentan is an amount (typically a daily amount administered over the course of a period of treatment) sufficient to provide any one or more of the effects mentioned above. Preferably the amount administered does not exceed an amount causing an unacceptable degree of adverse side effects.

What constitutes a therapeutically effective amount can vary depending on the particular pulmonary hypertension condition to be treated, the severity of the condition, body weight and other parameters of the individual subject, and can be readily established without undue experimentation by the physician or clinician based on the disclosure herein. Typically, a therapeutically effective amount will be found in the range of about 1 to about 25 mg/day, for example about 2 to about 15 mg/day, about 2.5 to about 10 mg/day, or about 2.5, about 3, about 3.5, about 4, about 4.5, about 5, about 6, about 7, about 8, about 9 or about 10 mg/day.

Such an amount can be administered each day, for example in individual doses administered once, twice, or three or more times a day. However, dosages stated herein on a per day basis should not be construed to require administration of the daily dose each and every day. For example, if the ambrisentan is provided in a suitably slow-release form, two or more daily dosage amounts can be administered at a lower frequency, e.g., as a depot every second day to once a month or even longer. Most typically and conveniently for the patient, ambrisentan is administered once a day, for example in the morning.

The ambrisentan can be administered for an extended treatment period. Typically, the longer the treatment continues, the greater and more lasting will be the benefits. Illustratively, the treatment period can be at least about one month, for example at least about 3 months, at least about 6 months or at least about 1 year. In some cases, administration can continue for substantially the remainder of the life of the subject.

In this and other embodiments, ambrisentan can be administered by any suitable route including oral, rectal, intranasal, intrapulmonary (e.g., by inhalation) or parenteral (e.g., intradermal, transdermal, subcutaneous, intramuscular or intravenous) routes. Oral administration is most convenient for the majority of subjects and can occur independently of meal times, i.e., with or without food.

The ambrisentan can be administered in monotherapy or in combination therapy as described in greater detail hereinbelow.

In various aspects of the first embodiment, the subject experiences, during or following the treatment period, at least one of (a) adjustment of one or more hemodynamic parameters indicative of the pulmonary hypertension condition towards a more normal level versus baseline;
(b) increase in exercise capacity versus baseline;
(c) lowering of BDI versus baseline;
(d) improvement of one or more quality of life parameters versus baseline; and/or
(e) movement to a lower WHO functional class.

Any suitable measure of exercise capacity can be used; a particularly suitable measure is obtained in a 6-minute walk test (6MWT), which measures how far the subject can walk in 6 minutes, i.e., the 6-minute walk distance (6MWD).

The Borg dyspnea index (BDI) is a numerical scale for assessing perceived dyspnea (breathing discomfort). It measures the degree of breathlessness after completion of the 6 minute walk test (6MWT), where a BDI of 0 indicates no breathlessness and 10 indicates maximum breathlessness.

In various aspects of the first embodiment, the ambrisentan can be administered in an amount effective to adjust one or more hemodynamic parameters indicative of the pulmonary hypertension condition towards a more normal level. In one such aspect, mean PAP is lowered, for example by at least about 3 mmHg, or at least about 5 mmHg, versus baseline. In another such aspect, PVR is lowered. In yet another such aspect, PCWP or LVEDP is raised.

In various aspects of the first embodiment, the ambrisentan can be administered in an amount effective to improve pulmonary function versus baseline. Any measure of pulmonary function can be used; illustratively 6MWD is increased or BDI is lowered.

In one such aspect, 6MWD is increased from baseline by at least about 10 m, for example at least about 20 m or at least about 30 m. In many instances, the method of the present embodiment will be found effective to increase 6MWD by as much as 50 m or even more.

In another such aspect, BDI, illustratively as measured following a 6MWT, is lowered from baseline by at least about 0.5 index points. In many instances, the method of the present embodiment will be found effective to lower BDI by as much as 1 full index point or even more.

The SF-36® health survey provides a self-reporting, multi-item scale measuring eight health parameters: physical functioning, role limitations due to physical health problems, bodily pain, general health, vitality (energy and fatigue), social functioning, role limitations due to emotional problems, and mental health (psychological distress and psychological well-being). The survey also provides a physical component summary and a mental component summary. For further detail see, for example, Ware: SF-36® Health Survey Update, http://www.sf-36.org/tools/sf36.shtml.

In various aspects of the first embodiment, the ambrisentan can be administered in an amount effective to improve quality of life of the subject, illustratively as measured by one or more of the health parameters recorded in an SF-36® survey. For example, an improvement versus baseline is obtained in at least one of the SF-36 physical health related parameters (physical health, role-physical, bodily pain and/or general health) and/or in at least one of the SF-36 mental health related parameters (vitality, social functioning, role-emotional and/or mental health). Such an improvement can take the form of an increase of at least 1, for example at least 2 or at least 3 points, on the scale for any one or more parameters.

The ambrisentan can be administered in monotherapy or in combination therapy with one or more additional drugs, for example, as described in greater detail hereinbelow.

In a second embodiment of the invention, a method is provided for improving the prognosis for a subject having a pulmonary hypertension condition. The method of this embodiment comprises administering to the subject ambrisentan at a dose and frequency and for a treatment period effective to provide (a) a reduction in probability of a clinical worsening event during the treatment period, and/or (b) a reduction from baseline in serum brain natriuretic peptide (BNP) concentration, wherein, at baseline, time from first diagnosis of the condition in the subject is not greater than about 2 years.

Time from first diagnosis, in various aspects of the second embodiment, can be, for example, not greater than about 1.5 years, not greater than about 1 year, not greater than about 0.75 year or not greater than about 0.5 year. In one aspect of the second embodiment, administration of ambrisentan can begin substantially immediately, for example, within about one month or within about one week, upon diagnosis.

In the method of the second embodiment, the ambrisentan is administered at a dose and frequency and for a period of treatment sufficient to provide one or both of the effects mentioned above. Preferably the dose administered does not exceed an amount causing an unacceptable degree of adverse side effects. The dose administered can vary depending on the particular pulmonary hypertension condition to be treated, the severity of the condition, body weight and other parameters of the individual subject, and can be readily established without undue experimentation by the physician or clinician based on the disclosure herein.

Typically, a suitable daily dose will be found in the range of about 1 to about 25 mg/day, for example about 2 to about 15 mg/day, about 2.5 to about 10 mg/day, or about 2.5, about 3, about 3.5, about 4, about 4.5, about 5, about 6, about 7, about 8, about 9 or about 10 mg/day. Such an amount can be administered each day, for example in individual doses administered once, twice, or three or more times a day. However, dosages stated herein on a per day basis should not be construed to require administration of the daily dose each and every day. For example, if the ambrisentan is provided in a suitably slow-release form, two or more daily dosage amounts can be administered at a lower frequency, e.g., as a depot every second day to once a month or even longer. Most typically and conveniently for the patient, ambrisentan is administered once a day, for example in the morning.

In the method of the second embodiment, the treatment period is long enough for the stated effect to be produced. Typically, the longer the treatment continues, the greater and more lasting will be the benefits. Illustratively, the treatment period can be at least about one month, for example at least about 3 months, at least about 6 months or at least about 1 year. In some cases, administration can continue for substantially the remainder of the life of the subject.

In various aspects of the second embodiment, the ambrisentan can be administered in monotherapy or in combination therapy as described in greater detail hereinbelow.

In a particular aspect of the second embodiment, the method is effective to provide a reduction of at least about 25%, for example at least about 50%, at least about 75% or at least about 80%, in probability of a clinical worsening event during the treatment period.

Clinical worsening event (CWEs) include death, lung transplantation, hospitalization for the pulmonary hypertension condition, atrial septostomy, initiation of additional pulmonary hypertension therapy or an aggregate thereof. Therefore, the present embodiment provides a method effective to provide a reduction of at least about 25%, for example at least about 50%, at least about 75% or at least about 80%, in probability of death, lung transplantation, hospitalization for pulmonary arterial hypertension, atrial septostomy and/or initiation of additional pulmonary hypertension therapy during the treatment period.

Time to clinical worsening of the pulmonary hypertension condition is defined as the time from initiation of a ambrisentan treatment regime to the first occurrence of a CWE.

In another particular aspect of the second embodiment, the method is effective to provide a reduction from baseline of at least about 15%, for example at least about 25%, at least about 50% or at least about 75%, in BNP concentration.

The pulmonary hypertension condition according to the second embodiment can comprise any one or more of the conditions in the WHO or Venice (2003) classification described above. In one aspect of the second embodiment, the condition comprises PAH (WHO Group 1), for example idiopathic PAH, familial PAH or PAH associated with another disease.

In various aspects of the second embodiment, the subject at baseline exhibits PH (e.g., PAH) of at least WHO Class II, for example Class II, Class III or Class IV as described above.

In a more particular embodiment, the subject at baseline has a resting PAP of at least about 30 mmHg, for example at least about 35 mmHg or at least about 40 mmHg.

In various aspects of the second embodiment, the subject can experience, during or following the treatment period, at least one of
  (a) adjustment of one or more hemodynamic parameters indicative of improvement of the pulmonary hypertension condition towards a more normal level versus baseline;
  (b) improvement in pulmonary function; illustratively an increase in exercise capacity or lowering of BDI versus baseline;
  (c) improvement of one or more quality of life parameters versus baseline; and/or
  (d) maintenance of or movement to a lower WHO functional class.

For example, in one aspect the subject can experience improvement in pulmonary function versus baseline. Any measure of pulmonary function can be used; illustratively 6MWD is increased or BDI is lowered.

In one such aspect, 6MWD is improved from baseline by at least about 10 m, for example, at least about 20 m or at least about 30 m. In many instances, the method of the present embodiment will be found effective to increase 6MWD by as much as 50 m or even more.

In another such aspect, BDI, illustratively as measured following a 6MWT, is lowered from baseline by at least about 0.5 point. In many instances, the method of the present embodiment will be found effective to lower BDI by as much as 1 full index point or even more.

In another aspect, the subject can experience improvement in quality of life, illustratively as measured by one or more of the health parameters recorded in an SF-36® survey. For example, an improvement versus baseline can be obtained in at least one of the SF-36 physical health related parameters (physical health, role-physical, bodily pain and/or general health) and/or in at least one of the SF-35 mental health related parameters (vitality, social functioning, role-emotional and/or mental health). Such an improvement can take the form of an increase of at least 1, for example at least 2 or at least 3 points, on the scale for any one or more parameters.

In another aspect, the subject can experience maintenance or improvement in WHO functional class.

In a third embodiment, a method is provided for prolonging the life of a subject having a pulmonary hypertension condition, comprising administering to the subject ambrisentan at a dose and frequency and for a treatment period effective to increase life expectancy, from a time of initiation of treatment, by at least about 30 days, wherein, at baseline, time from first diagnosis of the condition in the subject is not greater than about 2 years. Variants and illustrative modalities of this method are as set forth for the second embodiment above.

In a fourth embodiment, a method is provided for extending time to clinical worsening in a subject having a pulmonary hypertension condition, comprising administering to the subject ambrisentan at a dose and frequency and for a treatment period effective to decrease the probability of a clinical worsening event by at least about 25%, wherein, at baseline, time from first diagnosis of the condition in the subject is not greater than about 2 years. Variants and illustrative modalities of this method are as set forth for the second embodiment above.

In any of the methods described hereinabove, the subject can be male or female. For example, ambrisentan can be administered to a female subject according to any of the above methods, including the indicated variants and illustrative modalities thereof. Alternatively, ambrisentan can be administered to a male subject, for example a reproductively active male subject, according to any of the above methods, including the indicated variants and illustrative modalities thereof.

In a fifth embodiment, a method is provided for treating a pulmonary hypertension condition in a reproductively active male subject, the method comprising administering a therapeutically effective amount of ambrisentan to the subject, wherein fertility of the subject is not substantially compromised. "Not substantially compromised" in the present context means that spermatogenesis is not substantially reduced by the treatment and that no hormonal changes are induced that are indicative of or associated with reduced spermatogenesis. Male fertility can be assessed directly, for example, by sperm counts from semen samples, or indirectly by changes in hormones such as follicle stimulating hormone (FSH), luteinizing hormone (LH), inhibin B and testosterone.

In accordance with the fifth embodiment of the invention, administration of ambrisentan as described hereinabove, including the indicated variants and illustrative modalities of such administration, has generated no evidence of an adverse effect on male fertility as directly or indirectly assessed.

In a sixth embodiment, a method is provided for treating PAH in a subject, comprising administering a therapeutically effective amount of ambrisentan to the subject, wherein the PAH is associated with one or more of (a) a congenital heart defect, (b) portal hypertension, (c) use of a drug or toxin other than an anorexigen, (d) thyroid disorder, (e) glycogen storage disease, (f) Gaucher disease, (g) hereditary hemorrhagic telangiectasia, (h) hemoglobinopathy, (i) myeloproliferative disorder, (j) splenectomy, (k) pulmonary veno-occlusive disease and/or (l) pulmonary capillary hemangiomatosis. Variants and illustrative modalities of this method are as set forth hereinabove.

In a seventh embodiment, a method is provided for treating a pulmonary hypertension condition classified in WHO Groups 2-5 in a subject, comprising administering a therapeutically effective amount of ambrisentan to the subject. Variants and illustrative modalities of this method are as set forth hereinabove.

In one aspect of the seventh embodiment, the condition comprises left-sided atrial or ventricular heart disease and/or left-sided valvular heart disease.

In another aspect of the seventh embodiment, the condition is associated with one or more of chronic obstructive pulmonary disease (COPD), interstitial lung disease (ILD), sleep-disordered breathing, an alveolar hypoventilation disorder, chronic exposure to high altitude, a developmental abnormality, thromboembolic obstruction of proximal and/or distal pulmonary arteries, a non-thrombotic pulmonary embolism, sarcoidosis, histiocytosis X, lymphangiomatosis, and/or compression of pulmonary vessels.

In all the above embodiments of the invention, the ambrisentan can be administered in monotherapy.

Alternatively, the ambrisentan can be administered in combination therapy with a second active agent effective for the treatment of the pulmonary hypertension condition or a condition related thereto. When ambrisentan is administered concomitantly, one of skill in the art can readily identify a suitable dose for any particular second active agent from publicly available information in printed or electronic form, for example on the internet. Illustratively and without limitation, the ambrisentan can be administered with a second active agent comprising at least one drug selected from the group consisting of prostanoids, phosphodiesterase inhibitors (especially phosphodiesterase-5 (PDE5) inhibitors), endothelin receptor antagonists (ERAs) other than ambrisentan, calcium channel blockers, diuretics, anticoagulants, oxygen and combinations thereof.

Examples of drugs useful in combination therapy with ambrisentan are classified and presented in several lists below. Some drugs are active at more than one target; accordingly certain drugs may appear in more than one list. Use of any listed drug in a combination is contemplated herein, independently of its mode of action.

A suitable prostanoid can be illustratively selected from the following list:
beraprost
cicaprost
epoprostenol
iloprost
NS-304
$PGE_1$
prostacyclin
treprostinil A suitable PDE5 inhibitor can illustratively be selected from the following list:

sildenafil
tadalafil
vardenafil

An ERA other than ambrisentan can illustratively be selected from the following list:
   atrasentan
   BMS 193884
   bosentan
   CI-1020
   darusentan
   S-0139
   SB-209670
   sitaxsentan
   TA-0201
   tarasentan
   TBC-3711
   VML-588
   ZD-1611

A suitable calcium channel blocker can illustratively be selected from the following list:
   Aryklalkylamines
   bepridil
   clentiazem
   diltiazem
   fendiline
   gallopamil
   mibefradil
   prenylamine
   semotiadil
   terodiline
   verapamil
   Dihydropyridine Derivatives
   amlodipine
   aranidipine
   barnidipine
   benidipine
   cilnidipine
   efonidipine
   elgodipine
   felodipine
   isradipine
   lacidipine
   lercanidipine
   manidipine
   nicardipine
   nifedipine
   nilvadipine
   nimodipine
   nisoldipine
   nitrendipine
   NZ 105
   Piperazine Derivatives
   cinnarizine
   dotarizine
   flunarizine
   lidoflazine
   lomerizine
   Unclassified
   bencyclane
   etafenone
   fantofarone
   monatepil
   perhexiline Particularly suitable calcium channel blockers include amlodipine, diltiazem, felodipine, isradipine, nicardipine, nifedipine, nisoldipine, verapamil and combinations thereof.

A suitable diuretic can illustratively be selected from the following list:
   Organomercurials
   chlormerodrin
   chlorothiazide
   chlorthalidone
   meralluride
   mercaptomerin sodium
   mercumatilin sodium
   mercurous chloride
   mersalyl
   Purines
   pamabrom
   protheobromine
   theobromine
   Steroids
   canrenone
   oleandrin
   spironolactone
   Sulfonamide Derivatives
   acetazolamide
   ambuside
   azosemide
   bumetanide
   butazolamide
   chloraminophenamide
   clofenamide
   clopamide
   clorexolone
   disulfamide
   ethoxzolamide
   furosemide
   mefruside
   methazolamide
   piretanide
   torsemide
   tripamide
   xipamide
   Thiazides and Analogs
   althiazide
   bendroflumethiazide
   benzthiazide
   benzylhydrochlorothiazide
   buthiazide
   chlorthalidone
   cyclopenthiazide
   cyclothiazide
   ethiazide
   fenquizone
   hydrochlorothiazide
   hydroflumethiazide
   indapamide
   methyclothiazide
   metolazone
   paraflutizide
   polythiazide
   quinethazone
   teclothiazide
   trichlormethiazide
   Uracils
   aminometradine
   Unclassified
   amiloride
   Biogen BG 9719
   chlorazanil
   ethacrynic acid
   etozolin isosorbide
Kiowa Hakko KW 3902
mannitol
muzolimine
perhexyline
Sanofi-Aventis SR 121463
ticrynafen
triamterene
urea In some embodiments, the diuretic if present comprises a thiazide or loop diuretic. Thiazide diuretics are generally not preferred where the patient has a complicating condition such as diabetes or chronic kidney disease, and in such situations a loop diuretic can be a better choice.

Particularly suitable thiazide diuretics include chlorothiazide, chlorthalidone, hydrochlorothiazide, indapamide, metolazone, polythiazide and combinations thereof. Particularly suitable loop diuretics include bumetanide, furosemide, torsemide and combinations thereof.

A suitable anticoagulant can illustratively be selected from the following list:
acenocoumarol
ancrod
anisindione
bromindione
clorindione
coumetarol
cyclocumarol
dextran sulfate sodium
dicumarol
diphenadione
ethyl biscoumacetate
ethylidene dicoumarol
fluindione
heparin
hirudin
lyapolate sodium
pentosan polysulfate
phenindione
phenprocoumon
phosvitin
picotamide
tioclomarol
warfarin Where the pulmonary hypertension condition is associated with an underlying disease (for example CTD, HIV infection, COPD or ILD), ambrisentan can optionally be administered in combination therapy with one or more drugs targeting the underlying condition.

When ambrisentan is used in combination therapy with one or more drugs, the ambrisentan and at least one drug can be administered at different times or at about the same time (at exactly the same time or directly one after the other in any order). The ambrisentan and the second active drug can be formulated in one dosage form as a fixed-dose combination for administration at the same time, or in two or more separate dosage forms for administration at the same or different times.

Separate dosage forms can optionally be co-packaged, for example in a single container or in a plurality of containers within a single outer package, or co-presented in separate packaging ("common presentation"). As an example of co-packaging or common presentation, a kit is contemplated comprising, in separate containers, ambrisentan and at least one drug useful in combination with the ambrisentan. In another example, the ambrisentan and the at least one drug useful in combination therapy with the ambrisentan are separately packaged and available for sale independently of one another, but are co-marketed or co-promoted for use according to the invention. The separate dosage forms can also be presented to a patient separately and independently, for use according to the invention.

Typically at least the ambrisentan is provided in an orally deliverable formulation, for example a formulation adapted for oral delivery of a ambrisentan dose of about 1 to about 600 mg/day, e.g., about 10 to about 300 mg/day. The ambrisentan formulation can be adapted for any suitable frequency of administration, but in one embodiment is adapted for once a day oral administration.

In one embodiment at least one of the drugs other than ambrisentan in the combination is provided in an orally deliverable formulation; for example, each of the drugs can be so provided, and each of the drugs can be in a formulation adapted for once a day oral administration. Each of the drugs other than ambrisentan is typically present in the combination in an amount providing an adequate to full dose of the drug. One of skill in the art can readily identify a suitable dose for any particular drug from publicly available information in printed or electronic form, for example on the internet.

Any two or more drugs in the combination can optionally be coformulated to provide a fixed dose combination. For example, the ambrisentan can be coformulated with any one or more of the other drugs in the combination.

Mention of a particular drug or second active agent in the present specification and claims will be understood, except where the context demands otherwise, to include pharmaceutically acceptable salts, esters, prodrugs, metabolites, racemates and enantiomers of the drug, to the extent that such salts, esters, prodrugs, metabolites, racemates or enantiomers exist and are therapeutically effective.

EXAMPLES

The following examples are merely illustrative, and do not limit this disclosure in any way. Reference is made in the examples to statistical analysis and statistical significance of results. Such reference is made in the interest of full disclosure and does not constitute admission that statistical significance is a prerequisite for patentability of any claim herein. Reference is also made to "primary" and "secondary" endpoints or objectives of particular clinical trials. These endpoints or objectives should not necessarily be considered "primary" or "secondary" with respect to the present invention.

Examples 1 and 2 relate to Phase III clinical trials known as ARIES-2 and ARIES-1, respectively. Certain results and other information relating to these trials have been mentioned in the following news releases and presented at various conferences as announced in some of these news releases. Each of the documents individually cited immediately below is incorporated by reference in its entirety herein without admission that any such document represents prior art to the present invention.

Myogen, Inc. News Release, Dec. 12, 2005 (http://investor.myogen.com/phoenix.zhtml?c=135160&p=irol-newsArticle&ID=794738 &highlight=).

Myogen, Inc. News Release, Feb. 13, 2006 (http://investor.myogen.com/phoenix.zhtml?c=135160&p=irol-newsArticle&ID=815989 &highlight=).

Myogen, Inc. News Release, Mar. 2, 2006 (http://investor.myogen.com/phoenix.zhtml?c=135160&p=irol-newsArticle&ID=824548&highlight=) and ATS May 19-24, 2006 presentation announced therein.

Myogen, Inc. News Release, Apr. 10, 2006 (http://investor.myogen.com/phoenix.zhtml?c=135160&p=irol-newsArticle&ID=840536&highlight=).

Myogen, Inc. News Release, May 3, 2006 (http://investor.myogen.com/phoenix.zhtml?c=135160&p=irol-newsArticle&ID=851641&highlight=).

Myogen, Inc. News Release, May 8, 2006 (http://investor.myogen.com/phoenix.zhtml?c=135160&p=irol-newsArticle&ID=853198&highlight=).

Myogen, Inc. News Release, May 24, 2006 (http://investor.myogen.com/phoenix.zhtml?c=135160&p=irol-newsArticle&ID=860158&highlight=) and ATS 2006 presentation by Olschewski announced therein.

Myogen, Inc. News Release, Aug. 7, 2006 (http://investor.myogen.com/phoenix.zhtml?c=135160&p=irol-newsArticle&ID=892987&highlight=).

Myogen, Inc. News Release, Sep. 5, 2006 (http://investor.myogen.com/phoenix.zhtml?c=135160&p=irol-newsArticle&ID=902050&highlight=) and World Congress of Cardiology (Sep. 2-6, 2006, Barcelona, Spain) presentation by Galié announced therein; also abstract of Galié presentation at http://cic.escardio.org/AbstractDetails.aspx?id=41830&eevtid=15.

Myogen, Inc. News Release, Oct. 10, 2006 (http://investor.myogen.com/phoenix.zhtml?c=135160&p=irol-newsArticle&ID=913787&highlight=) and CHEST 2006 presentation by Oudiz announced therein.

Myogen June 2006 presentation available at library.corporate-ir.net/library/13/135/135160/items/203236/Junepresentation.pdf.

Example 1

Summary

The primary objective of this study was to determine the effect of ambrisentan on exercise capacity in subjects with PAH. The secondary objectives of this study were to evaluate effects of ambrisentan on other clinical measures of PAH, as well as safety and tolerability of the study drug.

Study drug was provided in round, biconvex, oral tablets that were identical in appearance. Three strengths of active study drug, containing 1 mg, 2.5 mg or 5 mg of ambrisentan, were used in this study. All study drug was packaged in blister cards. Subjects were instructed to take study drug once daily (q.d.) by mouth (p.o.) in the morning, with or without food.

The maximum study duration was up to 14 weeks from the time of initial screening procedures to the final study visit (Week 12). Screening procedures were performed a maximum of 2 weeks prior to the first dose of study drug. The maximum duration of study drug treatment was 12 weeks.

Placebo was indistinguishable from active treatment.

Methods (Example 1)

Patients

The number of subjects enrolled was 192 at 41 investigative sites.

Men and women, 18 years of age or older, with idiopathic PAH, PAH associated with connective tissue disease (CTD), e.g., mixed CTD, CREST syndrome, systemic sclerosis (scleroderma), overlap syndrome or systemic lupus erythematosus, or PAH associated with anorexigen use or HIV infection were enrolled in this study. Subjects were to have a documented mean PAP≧25 mmHg, PVR>3 mmHg/L/min, and PCWP or LVEDP<15 mmHg. Subjects must have been able to walk a distance of at least 150 m but no more than 450 m during 2 consecutive 6MWTs to be eligible for inclusion in the study.

Study Design and Treatment

After a 2 week screening period, eligible subjects were stratified based on the underlying etiology of PAH (idiopathic or non-idiopathic) and were randomized to 1 of 3 treatment groups (placebo, 2.5 mg or 5 mg ambrisentan) in a ratio of 1:1:1. One blinded dose reduction was permitted during the 12-week treatment period in the event of study drug intolerance (e.g., 5 mg to 2.5 mg, 2.5 mg to 1 mg, placebo to placebo). Subjects received a daily dose of 1 mg ambrisentan only if they reduced from the 2.5 mg dose group. Subjects were assessed for efficacy and safety at monthly intervals.

Due to the placebo-controlled design of this study, there was a 1 in 3 chance that a subject did not receive ambrisentan for a period of 12 weeks. Therefore, after a minimum treatment period of 4 weeks, subjects who met 2 or more of the following predefined early escape criteria may have been removed from the study:

(a) a decrease from baseline of at least 20% in 6MWD;
(b) an increase of 1 or more WHO functional class;
(c) worsening right ventricular failure (e.g., as indicated by increased jugular venous pressure, new or worsening hepatomegaly, ascites or peripheral edema);
(d) rapidly progressing cardiogenic, hepatic or renal failure; and/or
(e) refractory systolic hypotension (systolic blood pressure <85 mmHg).

Subjects receiving placebo who were removed from the study due to 2 or more early escape criteria were eligible to enter a long-term extension study, and receive active treatment with ambrisentan.

Serum levels of alanine aminotransferase (ALT), aspartate aminotransferase (AST), alkaline phosphatase, gamma-glutamyl transpeptidase (GGT) and total bilirubin were closely monitored in all subjects throughout the study. Female subjects of childbearing potential were required to undergo monthly pregnancy tests and to use a double method of contraception to reduce risk of pregnancy during the course of the study. Male subjects were required to undergo complete semen and hormone analyses to evaluate potential effects of ambrisentan on male fertility.

After completion of the 12-week study, subjects were eligible to enroll into the long-term extension study.

Efficacy Assessments

The primary efficacy endpoint was change from baseline in 6MWD evaluated after 12 weeks of treatment compared to placebo.

The secondary efficacy endpoints included:

(a) time to clinical worsening of PAH, as defined by the time from randomization to the first occurrence of death, lung transplantation, hospitalization for PAH, atrial septostomy, study discontinuation due to addition of other PAH therapeutic agents, or study discontinuation due to 2 or more early escape criteria;
(b) change from baseline measured after 12 weeks of treatment compared to placebo in:
  (i) WHO functional class;
  (ii) SF-36® health survey physical functioning scale;
  (iii) BDI immediately following exercise; and/or
  (iv) an assessment of the safety and tolerability of the study drug; and
(c) change from baseline measured after 12 weeks of treatment compared to placebo in plasma levels of ET-1, cTnT and BNP.

Safety Assessments

All adverse effects (AEs) reported during the course of the study were reported and summaries of all AEs were prepared showing frequencies and percentages of:

(a) subjects with at least 1 AE;

(b) subjects with possibly or probably drug-related AEs;
(c) subjects with at least 1 serious AE (SAE);
(d) subjects with an AE leading to study discontinuation; and
(e) subjects who died.

Liver function test (LFT) assessments were separately summarized by severity relative to the upper limit of normal (ULN) for ALT, AST, alkaline phosphatase and total bilirubin.

For subjects who were on anticoagulants at any point during the study (regular visit or between visits), coagulation tests (prothrombin time (PT), partial thromboplastin time (PTT) and international normalized ratio (INR)) were completed. In addition to summary statistics by study visit, changes in PT and INR were examined relative to changes in warfarin-type anticoagulant dose. These analyses focused on the values at Week 0 and Week 12 and the percentage change from Week 0 to Week 12.

The results of semen samples and their normality or abnormality were assessed by an independent male fertility expert and summarized through frequency counts and percentages by treatment. Descriptive statistics for male hormone data were prepared by treatment for the Week 0 and Week 12 visits when data were collected. Change from Week 0 to Week 12 was determined. The male fertility hormone results were analyzed in combination with the semen sample results by a second independent male fertility expert.

Frequency counts and percentages were used to summarize frequency of normal, abnormal but not clinically significant, and abnormal and clinically significant electrocardiogram (ECG) results for each scheduled assessment time by treatment. All ECG data were digitally recorded and analyzed by a central reader. The following variables were analyzed: heart rate, RR and PR intervals, QRS duration, QT interval, QTcB, QTcF and ECG diagnostic variables. Descriptive statistics were used to summarize ECG results by treatment group and by week of ECG assessment.

Descriptive statistics for vital signs were reported for each scheduled assessment time by treatment and for the change from pre-dose Week 0 to each subsequent scheduled assessment by treatment.

Statistical Methods

A test of the null hypothesis of no treatment group difference in change from baseline in 6MWD with 62 subjects per group had approximately 90% power to detect an average placebo-adjusted treatment effect of 35 m based on a 2-sample t-test and a standard deviation of 55 m.

The intention-to-treat (ITT) population was defined as all randomized subjects who received at least 1 dose of study drug. For the ITT population, subjects were considered as belonging to their randomized treatment group, regardless of the actual treatment received.

The safety population was defined as all randomized subjects who received at least 1 dose of study drug. Subjects were considered as belonging to a treatment group according to the highest actual treatment dose received. Any subject who received 5 mg ambrisentan on any day was included in the 5 mg group for safety analyses in the entire study. Any subject who received 2.5 mg ambrisentan on any day and never received 5 mg ambrisentan on any day was included in the 2.5 mg group for safety analyses in the entire study. Otherwise, any subject who received only placebo was included in the placebo group for safety analyses in the study.

The primary efficacy endpoint was the change from baseline in 6MWD evaluated after 12 weeks of treatment compared to placebo, where the last observation was carried forward. Baseline 6MWD was defined as the mean 6MWD of the last two 6MWTs prior to randomization.

Change from baseline for Weeks 4, 8 and 12 in each of the two ambrisentan treatment groups were compared to placebo. The mean change was reported with 2-sided 95% confidence intervals (CIs) calculated by normal theory. The primary comparison was the change from baseline to Week 12. The Wilcoxon rank sum test stratified by idiopathic and non-idiopathic PAH subjects was used for inference. A fixed sequence approach was used to control the type I error rate accounting for the two comparisons. The higher dose was first compared to placebo. Because the p-value from the Wilcoxon rank sum test was less than 0.05 for the 5 mg ambrisentan group, the difference was considered significant, and the lower dose was compared to placebo, again at the full 0.05 $\alpha$-level.

The two ambrisentan dose groups were also combined and compared to the placebo group. A p-value was reported, but for descriptive purposes only, with no impact on the fixed sequence procedure used for comparing the two individual dose groups to the placebo group.

If both ambrisentan dose groups were superior to placebo for the primary endpoint, evaluation of the secondary endpoints was done by combining the subjects from the two dose groups for comparison to the placebo group. However, if only the 5 mg group was significant for the primary endpoint, evaluation of the secondary endpoints was done only for that dose group. Secondary endpoint analyses were stratified by idiopathic and non-idiopathic PAH subjects.

The two most important secondary endpoints, time to clinical worsening of PAH and change in WHO functional class, were compared to placebo using a weighted version of Hommel's extension of the Simes test, with an overall $\alpha$ of 0.05. Time to clinical worsening was assigned a weight of 80% while change in WHO functional class received 20% of the weight. These two tests served as a gatekeeper, allowing the physical functioning scale of the SF-36® health survey to be tested if at least one of the first two secondary endpoints was significant. Lastly, the BDI was tested conditional on a significant result from the test of the SF-36® physical functioning scale.

Analyses of ET-1, cTnT, and BNP plasma levels were performed both for change from baseline (treatment effect) and baseline impact on efficacy. Descriptive statistics were presented for the change from pre-dose Week 0 to Week 12 by treatment.

Results (Example 1)
Patients (Study Population)

Disposition of randomized subjects is shown in Table 1.1.

TABLE 1.1

| | Subject disposition (% of randomized subjects) | | | |
|---|---|---|---|---|
| | Placebo (N = 65) | 2.5 mg ambrisentan (N = 64) | 5 mg ambrisentan (N = 63) | Combined ambrisentan (N = 127) |
| Randomized | 65 (100.0) | 64 (100.0) | 63 (100.0) | 127 (100.0) |
| Completed | 54 (83.1) | 58 (90.6) | 58 (92.1) | 116 (91.3) |
| Withdrew | 11 (16.9) | 6 (9.4) | 5 (7.9) | 11 (8.7) |
| Reasons for withdrawal: | | | | |
| Adverse event | 3 (4.6) | 1 (1.6) | 3 (4.8) | 4 (3.1) |
| Clinical status did not improve or deteriorated | 1 (1.5) | 0 (0.0) | 0 (0.0) | 0 (0.0) |

TABLE 1.1-continued

Subject disposition (% of randomized subjects)

|  | Placebo (N = 65) | 2.5 mg ambrisentan (N = 64) | 5 mg ambrisentan (N = 63) | Combined ambrisentan (N = 127) |
|---|---|---|---|---|
| Withdrawal of consent | 0 (0.0) | 3 (4.7) | 1 (1.6) | 4 (3.1) |
| Early escape | 7 (10.8) | 2 (3.1) | 1 (1.6) | 3 (2.4) |

A total of 192 subjects, with a mean age of 50.9 years, received at least 1 dose of study drug and were included in the ITT and safety populations. A majority of the subjects enrolled were female (74.5%) and Caucasian (84.9%). Approximately half (51.6%) of the subjects were residents of western Europe or Israel. The remainder of subjects was evenly distributed throughout eastern Europe (24.0%) and South America (24.5%).

The number of years that PAH was present prior to participation in the study was calculated from the date that PAH was diagnosed until the date that informed consent was signed. For subjects who had a diagnosis of PAH confirmed at the screening visit for this study, the number of years of PAH present prior to this study was set to zero. The mean number of years that PAH was present prior to participation in this study was similar for the placebo (2.3±4.22 years) and 5 mg (2.9±6.10 years) groups but longer than that of the 2.5 mg (1.2±1.93 years) group. The median number of years that PAH was present was less than 1 year for each treatment group: placebo, 0.38 years; 2.5 mg, 0.43 years; 5 mg, 0.26 years.

Of the subjects enrolled, 65% had a diagnosis of idiopathic PAH prior to enrollment, and 35% had PAH associated with CTD, anorexigen use or HIV infection (collectively designated non-idiopathic PAH herein); idiopathic and non-idiopathic PAH subjects were equally distributed between the treatment groups. Nearly all of the subjects had either WHO functional class II (44.8%) or class III (51.6%) symptoms. The mean (±standard deviation (SD)) baseline 6MWD for all subjects was 348.4±84.46 m.

In general, demographic and baseline characteristics of the subjects participating were well balanced between the treatment groups. There was a difference in baseline 6MWD between subjects with WHO functional class II and WHO class III symptoms for both the placebo and combined ambrisentan groups: class II, 372.0 m and 379.1 m and class III, 330.2 m and 328.2 m, respectively.

The most frequently used concomitant medications were furosemide (37.0%), acenocoumarol (28.6%) and spironolactone (25.0%). There did not appear to be any differences in concomitant medication use across the treatment groups.

Efficacy of Ambrisentan

Change in 6MWD from baseline to Week 12 in the ITT population is shown in Table 1.2.

TABLE 1.2

Change in 6MWD, meters

|  | Placebo | 2.5 mg ambrisentan | 5 mg ambrisentan | Combined ambrisentan |
|---|---|---|---|---|
| Baseline 6MWD, mean (SD) | 342.7 (85.93) | 347.3 (83.81) | 355.3 (84.45) | 351.3 (83.89) |
| Week 12 6MWD, mean (SD) | 332.6 (130.42) | 369.6 (128.31) | 404.7 (99.45) | 387.0 (115.80) |

TABLE 1.2-continued

Change in 6MWD, meters

|  | Placebo | 2.5 mg ambrisentan | 5 mg ambrisentan | Combined ambrisentan |
|---|---|---|---|---|
| Change from baseline to Week 12, mean (SD) | −10.1 (93.79) | +22.2 (82.67) | +49.4 (75.36) | +35.7 (79.99) |

The primary efficacy endpoint was statistically significant for both doses of ambrisentan compared to placebo. The placebo-adjusted improvement in mean 6MWD at Week 12 was +59.4 m (95% CI: +29.6 to +89.3 m; p<0.001) for the 5 mg group and +32.3 m (95% CI: +1.5 to +63.1 m; p=0.022) for the 2.5 mg group. For subjects in the placebo group, mean 6MWD showed a decrease from baseline (−10.1 m). For subjects receiving ambrisentan, improvement in 6MWD compared to placebo was observed as early as Week 8, and by Week 12 there was evidence of a dose response.

The key secondary endpoint of time to clinical worsening of PAH demonstrated that ambrisentan (combined ambrisentan group) significantly delayed the time to clinical worsening of PAH compared to placebo (p<0.001). In the placebo group, 21.5% of subjects experienced an event of clinical worsening compared to 4.7% and 4.8% of subjects in the 2.5 mg and 5 mg dose groups, respectively. Furthermore, the hazard ratio demonstrated an 80% reduction in the probability of clinical worsening occurring at any given time for a subject receiving ambrisentan, when compared to placebo.

The time to clinical worsening of PAH is displayed in FIG. 1 as a Kaplan-Meier event-free curve through Week 12 for each treatment group in the ITT population.

A summary of events defining clinical worsening by treatment group is presented in Table 1.3.

TABLE 1.3

Clinical worsening events (% of ITT population)

| Event | Placebo (N = 65) | 2.5 mg ambrisentan (N = 64) | 5 mg ambrisentan (N = 63) | Combined ambrisentan (N = 127) |
|---|---|---|---|---|
| Death | 3 (4.6) | 2 (3.1) | 0 (0.0) | 2 (1.6) |
| Lung transplantation | 0 (0.0) | 0 (0.0) | 0 (0.0) | 0 (0.0) |
| Hospitalization for PAH | 9 (13.8) | 3 (4.7) | 2 (3.2) | 5 (3.9) |
| Atrial septostomy | 0 (0.0) | 0 (0.0) | 0 (0.0) | 0 (0.0) |
| Study withdrawal due to addition of PAH treatment | 0 (0.0) | 0 (0.0) | 0 (0.0) | 0 (0.0) |
| Escape criteria | 7 (10.8) | 2 (3.1) | 1 (1.6) | 3 (2.4) |
| Total subjects with ≧1 event | 14 (21.5) | 3 (4.7) | 3 (4.8) | 6 (4.7) |

Of the 9 (13.8%) subjects in the placebo group hospitalized for PAH, 5 were hospitalized for right heart failure or worsening right heart failure. Comparatively, 5 (3.9%) subjects receiving ambrisentan were hospitalized for PAH, of whom 1 (in the 5 mg dose group) was hospitalized for worsening right heart failure.

There were a total of 6 deaths reported during this study or within 30 days of the last dose of study drug. In the placebo group, 4 (6.2%) subjects died, and 2 (3.1%) subjects in the 2.5 mg dose group died. No subjects receiving 5 mg ambrisentan died during the 12-week study. Five of the 6 deaths were captured as clinical worsening events; 3 (4.6%) placebo subjects and 2 (3.1%) subjects receiving 2.5 mg ambrisentan died prior to completion of the 12-week treatment period. The sixth subject who dies was in the placebo group. This subject was hospitalized for clinical worsening of PAH, and the date of hospitalization was captured as the date of clinical worsening for this subject. The subject discontinued the study via the early escape procedure and subsequently died.

Change in WHO functional class from baseline to Week 12 in the ITT population is shown in Table 1.4.

TABLE 1.4

Change in WHO functional class (% of ITT population)

| Change (no. of classes) | Placebo (N = 65) | 2.5 mg ambrisentan (N = 64) | 5 mg ambrisentan (N = 63) | Combined ambrisentan (N = 127) |
| --- | --- | --- | --- | --- |
| −2 | 0 (0.0) | 0 (0.0) | 1 (1.6) | 1 (0.8) |
| −1 | 11 (16.9) | 10 (15.6) | 8 (12.7) | 18 (14.2) |
| no change | 42 (64.6) | 51 (79.7) | 52 (82.5) | 103 (81.1) |
| +1 | 10 (15.4) | 2 (3.1) | 2 (3.2) | 4 (3.1) |
| +2 | 2 (3.1) | 1 (1.6) | 0 (0.0) | 1 (0.8) |

A statistically significant difference between treatment groups in the change in WHO functional class was not observed at Week 12. However, a more than 4-fold greater percentage of subjects in the placebo group (18.5%) deteriorated by at least 1 WHO class compared to subjects in the combined ambrisentan group (3.9%).

The percentage of subjects at least maintaining their baseline WHO functional class at Week 12 was 81.5% in the placebo group, 95.3% in the 2.5 mg dose group and 96.8% in the 5 mg dose group.

Change in SF-36® health survey parameters from baseline to Week 12 is shown in Table 1.5.

TABLE 1.5

Change in SF-36 ® health survey parameters, mean (SD)

| Parameter | Placebo | 2.5 mg ambrisentan | 5 mg ambrisentan | Combined ambrisentan |
| --- | --- | --- | --- | --- |
| Physical functioning | −0.20 (7.14) | +3.86 (7.14) | +2.96 (6.81) | +3.41 (6.96) |
| Role-physical | −0.15 (10.04) | +5.87 (11.72) | +7.61 (10.41) | +6.74 (11.07) |
| Bodily pain | −0.24 (12.02) | +2.34 (11.87) | +0.46 (9.99) | +1.40 (10.96) |
| General health | +1.37 (6.24) | +3.84 (6.71) | +4.95 (8.05) | +4.40 (7.40) |
| Vitality | −0.01 (9.11) | +4.07 (9.12) | +5.21 (8.79) | +4.64 (8.94) |
| Social functioning | +2.45 (10.54) | +4.55 (9.72) | +4.85 (11.89) | +4.70 (10.81) |
| Role-emotional | −1.58 (14.25) | +3.11 (12.90) | +8.15 (14.43) | +5.63 (13.86) |
| Mental health | +2.53 (10.79) | +4.98 (9.70) | +4.03 (10.13) | +4.50 (9.88) |
| Physical component summary | −0.15 (7.29) | +3.78 (7.63) | +2.97 (7.79) | +3.38 (7.69) |
| Mental component summary | +1.27 (11.29) | +4.05 (10.30) | +6.28 (11.64) | +5.17 (11.00) |

A statistically significant increase was observed for the combined ambrisentan group (3.41±6.96) in the physical functioning scale of the SF-36® health survey compared to placebo (−0.20±8.14, p=0.005). Improvements in the physical functioning scale were also demonstrated for both the 2.5 mg and 5 mg dose groups compared to placebo. Furthermore, increases were observed in several other SF-36® scales including role-physical, general health, vitality and role-emotional scales.

A statistically significant improvement in BDI was observed at Week 12 for the combined ambrisentan group, with a placebo-adjusted BDI of −1.1 (95% CI: −1.8 to −0.4; p=0.019). Improvements in BDI were observed for both the 2.5 mg and 5 mg dose groups compared to placebo. For subjects in the placebo group, mean BDI increased (worsened) from baseline by +0.82. In contrast, in the 2.5 mg and 5 mg ambrisentan dose groups mean BDI decreased (improved) from baseline (−0.20 and −0.36, respectively).

At Week 12, the geometric mean percent change in plasma ET-1 decreased by 4% (95% CI: 0.68 to 1.36) in the placebo group; whereas the geometric mean percent change in plasma ET-1 increased from baseline by 19% (95% CI: −12% to 61%; p=0.193 versus placebo) in the 2.5 mg group and by 72% (95% CI: 32% to 125%; p=0.004 versus placebo) in the 5 mg group. The change from baseline was substantially greater than placebo for the 5 mg group, but not for the 2.5 mg group.

At baseline, approximately 90% of plasma cTnT concentrations were below the level of quantification (0.01 ng/ml). Changes in cTnT concentrations during the 12-week study were minor and not remarkably different from zero.

At Week 12, the geometric mean percent change plasma BNP increased by 13% (95% CI: −6% to 36%) in the placebo group. In contrast, the geometric mean plasma BNP decreased from baseline by 29% (95% CI: −44% to −9%; p=0.002 versus placebo) in the 2.5 mg group and by 30% (95% CI: −47% to −9%; p=0.002 versus placebo) in the 5 mg group. The decrease from baseline was substantially greater than placebo for the 2.5 mg group and the 5 mg group.

Efficacy by Subgroup

Improvements in 6MWD were observed for both WHO functional class I/II and WHO functional class III/IV subjects at Week 12. For the class I/II subgroup, the placebo-adjusted 6MWD increase from baseline at Week 12 was +44.1 m and +67.7 m for the 2.5 mg and 5 mg dose groups, respectively. For the class III/IV subgroup, the placebo-adjusted 6MWD increase from baseline at Week 12 was +17.6 m and +51.8 m for the 2.5 mg and 5 mg dose groups, respectively.

Improvements in 6MWD at Week 12 were observed in both ambrisentan dose groups for the idiopathic PAH subgroup and in the 5 mg dose group for the non-idiopathic PAH subgroup. For the idiopathic PAH subgroup, the placebo-adjusted 6MWD increase from baseline at Week 12 was +56.3 m and +75.7 m for the 2.5 mg and 5 mg dose groups, respectively. For the non-idiopathic PAH subgroup, the placebo-adjusted 6MWD change from baseline at Week 12 was −12.6 m and +29.5 m for the 2.5 mg and 5 mg dose groups, respectively.

Improvements in 6MWD at Week 12 were observed in both ambrisentan dose groups for the female subjects. For female subjects, the placebo-adjusted 6MWD increase from baseline at Week 12 was +42.5 m and +75.7 m for the 2.5 mg and 5 mg dose groups, respectively. For male subjects, the placebo-adjusted 6MWD change from baseline at Week 12 was +6.8 m and +2.7 m for the 2.5 mg and 5 mg dose groups, respectively.

Improvements in 6MWD at Week 12 were observed in both ambrisentan dose groups for the eastern European and South American populations and in the 5 mg dose group for the western European/Israel population. For the eastern European subgroup, the placebo-adjusted 6MWD increase from baseline at Week 12 was +66.1 and +88.0 m for the 2.5 mg and 5 mg dose groups respectively. For the South American subgroup, the placebo-adjusted 6MWD increase from baseline at Week 12 was +50.5 and +79.5 m for the 2.5 mg and 5 mg dose groups respectively. For the western European/Israel subgroup, the placebo-adjusted 6MWD increase from baseline at Week 12 was +3.0 and +39.4 m for the 2.5 mg and 5 mg dose groups, respectively.

Safety Results

A summary of adverse events recorded is shown in Table 1.6.

TABLE 1.6

Global summary of adverse events (% of safety population)

| Subjects | Placebo (N = 65) | 2.5 mg ambrisentan (N = 64) | 5 mg ambrisentan (N = 63) | Combined ambrisentan (N = 127) |
|---|---|---|---|---|
| with at least 1 AE | 52 (80.0) | 47 (73.4) | 46 (73.0) | 93 (73.2) |
| with at least 1 related AE | 22 (33.8) | 19 (29.7) | 21 (33.3) | 40 (31.5) |
| with at least 1 SAE | 15 (23.1) | 8 (12.5) | 6 (9.5) | 14 (11.0) |
| with an AE leading to study discontinuation | 6 (9.2) | 3 (4.7) | 4 (6.3) | 7 (5.5) |
| who discontinued the study via early escape | 7 (10.8) | 2 (3.1) | 1 (1.6) | 3 (2.4) |
| who died | 4 (6.2) | 2 (3.1) | 0 (0.0) | 2 (1.6) |

During this 12-week study, 80.0% of the subjects in the placebo group experienced at least 1 AE. Similarly, 73.4% of subjects in the 2.5 mg dose group and 73.0% of subjects in the 5 mg dose group experienced at least 1 AE during the study.

Overall, more subjects in the placebo group compared to the ambrisentan groups prematurely discontinued from the study due to death, SAEs, AEs, and/or the early escape procedure.

In general, more AEs were assessed as moderate and severe in the placebo group (43.1% and 18.5%, respectively) compared to the combined ambrisentan group (26.8% and 7.9%, respectively).

None of the 127 subjects who received ambrisentan developed any elevated serum aminotransferase concentrations >3.0×ULN, compared to 1 subject in the placebo group, and there were no notable mean changes from baseline at Week 12 for serum ALT and AST, and no differences between treatment groups. Furthermore, there was a notable decrease in mean total bilirubin and mean alkaline phosphatase that appeared to be dose-dependent.

Mean uric acid increased at Week 12 in the placebo group (+34.1 μmol/l); whereas there was a substantial mean decrease in uric acid (−19.1 μmol/l) in the combined ambrisentan group.

The analysis of male fertility hormones in combination with a limited number of subjects (n=6) providing serial semen samples did not suggest that ambrisentan was associated with an adverse effect on male reproductive potential.

More specifically, changes over baseline in follicle stimulating hormone (FSH) concentration at Week 12 were small, ranging from −0.25 IU/liter (placebo group) to +0.58 IU/liter (2.5 mg dose group). Although the baseline FSH concentrations for the placebo and 5 mg dose groups (7.6±8.34 IU/liter and 7.6±5.69 IU/liter, respectively) suggest possibility of some spermatogenic dysfunction prior to the first dose of study drug, the changes observed during the study were unlikely to be of substantial clinical relevance.

Minor increases in luteinizing hormone (LH) concentration, ranging from 0.16 to 0.58 IU/liter, were observed in all treatment groups, with no apparent difference between groups.

Increases from baseline in mean inhibin B concentration at Week 12 were observed for the placebo group (139.6±95.34 pg/ml) and the 5 mg dose group (131.2±98.77 pg/ml), but a decrease was observed in the 2.5 mg dose group (−43.2±36.52 pg/ml). Therefore, changes in inhibin B were not dose-dependent. Based on expert opinion, none of the mean inhibin B concentrations measured at baseline and Week 12 indicated presence or development of spermatogenic dysfunction.

Subjects in the placebo group had a minor increase (0.66±3.904 nmol/l) in testosterone concentration over the 12-week study; however, testosterone concentrations decreased in an apparently dose-dependent manner in subjects receiving ambrisentan (2.5 mg, −0.09±4.595 nmol/1; 5 mg, −2.61±6.962 nmol/l. The data were variable and the median values indicated little change. Furthermore, the Week 12 data did not represent a decrease below the lower range of normal (10.41 nmol/l).

Discussion (Example 1)

The ambrisentan treatment benefit observed by the primary and secondary endpoints of this study was robust, internally consistent, and clinically relevant.

Both doses demonstrated a statistically significant and clinically relevant improvement in 6MWD that was associated with a significant decrease in BDI. The improvement in 6MWD was nearly twice as large in the 5 mg dose group compared to the 2.5 mg dose group, and improvements in 6MWD were consistently dose-responsive for most subgroups evaluated. Furthermore, plasma BNP, a molecular marker that has been shown to decrease in patients with PAH who demonstrate improvements in 6MWD or hemodynamics, was substantially reduced with ambrisentan treatment. Ultimately, these symptomatic improvements resulted in a patient's self-assessment of an overall better quality of life, as measured by statistically significant improvements in several scales of the SF-36® health survey.

In addition to the symptomatic improvements observed for exercise capacity and dyspnea, there was a more than 4-fold greater percentage of subjects in the placebo group who deteriorated by at least 1 WHO class compared to subjects in the ambrisentan groups. Furthermore, there was a significant decrease in disease progression for subjects receiving ambrisentan compared to placebo as measured by the time to clinical worsening endpoint. This was associated with an 80% decrease in the risk of clinical worsening over the 12-week study for the ambrisentan group compared to placebo. The delay in disease progression was also apparent by the lower number of subjects in the ambrisentan treatment groups compared to placebo for each of the following safety categories: death, SAEs, AEs leading to discontinuation and early escapes. Finally, the most frequent AE observed in this study was right ventricular failure, an indicator of disease progression, which was reported in more than 3 times the percentage of subjects in the placebo group compared to the combined ambrisentan treatment group.

In general, ambrisentan was well tolerated, as demonstrated by the lack of dose reduction and AEs leading to discontinuation. The most frequent AEs of clinical concern observed for subjects receiving ambrisentan were headache and palpitations. For the most part, these events were mild in severity and did not lead to study discontinuation. Peripheral edema, which has been reported frequently with other ERAs was observed at a similar or lower frequency in the ambrisentan groups compared to placebo. None of the 127 subjects that received ambrisentan developed elevated serum aminotransferase concentrations >3×ULN, and there were no increases in mean ALT or AST concentrations for either ambrisentan dose group. Furthermore, there appeared to be a dose-dependent decrease in mean total bilirubin and mean alkaline phosphatase. Decreases in hemoglobin concentration were observed early in the study and did not decrease further with continued treatment.

In conclusion, the treatment benefits observed for the primary and secondary endpoints of this study were robust, internally consistent, and clinically relevant. Ambrisentan was well tolerated, was associated with a manageable safety profile, and delayed disease progression, indicating a positive risk-to-benefit profile.

Example 2

Summary

The primary objective of this study was to determine the effect of ambrisentan on exercise capacity in subjects with pulmonary arterial hypertension (PAH). The secondary objectives of this study were to evaluate effects of ambrisentan on other clinical measures of PAH, as well as safety and tolerability of the study drug.

Study drug was provided in round, biconvex, oral tablets that were identical in appearance. Three strengths of active study drug containing 2.5 mg, 5 mg or 10 mg of ambrisentan were used in this study. All study drug was packaged in blister cards. Subjects were instructed to take study drug once daily (q.d.) by mouth (p.o.) in the morning, with or without food.

The maximum study duration was up to 14 weeks from the time of initial screening procedures to the final study visit (Week 12). Screening procedures were performed a maximum of 2 weeks prior to the first dose of study drug. The maximum duration of study drug treatment was 12 weeks.

Placebo was indistinguishable from active treatment.

Methods (Example 2)

Patients

The number of subjects enrolled was 202 at 46 investigative sites.

Men and women, 18 years of age or older, with idiopathic PAH, PAH associated with CTD, e.g., mixed CTD, CREST syndrome, systemic sclerosis (scleroderma), overlap syndrome or systemic lupus erythematosus, or PAH associated with anorexigen use or HIV infection were enrolled in this study. Subjects were to have a documented mean PAP>25 mmHg, PVR>3 mmHg/L/min, and PCWP or LVEDP<15 mmHg. Subjects must have been able to walk a distance of at least 150 m but no more than 450 m during 2 consecutive 6MWTs to be eligible for inclusion in the study.

Study Design and Treatment

After a 2 week screening period, eligible subjects were stratified based on the underlying etiology of PAH (idiopathic or non-idiopathic) and were randomized to 1 of 3 treatment groups (placebo, 5 mg or 10 mg ambrisentan) in a ratio of 1:1:1. One blinded dose reduction was permitted during the 12-week treatment period in the event of study drug intolerance (e.g., 10 mg to 5 mg, 5 mg to 2.5 mg, placebo to placebo). Subjects received a daily dose of 2.5 mg ambrisentan only if they reduced from the 5 mg dose group. Subjects were assessed for efficacy and safety at monthly intervals.

Due to the placebo-controlled design of this study, there was a 1 in 3 chance that a subject did not receive ambrisentan for a period of 12 weeks. Therefore, after a minimum treatment period of 4 weeks, subjects who met 2 or more of the following predefined early escape criteria may have been removed from the study:

(a) a decrease from baseline of at least 20% in 6MWD;
(b) an increase of 1 or more WHO functional class;
(c) worsening right ventricular failure (e.g., as indicated by increased jugular venous pressure, new or worsening hepatomegaly, ascites or peripheral edema);
(d) rapidly progressing cardiogenic, hepatic or renal failure; and/or
(e) refractory systolic hypotension (systolic blood pressure <85 mmHg).

Subjects receiving placebo who were removed from the study due to 2 or more early escape criteria were eligible to enter a long-term extension study, and receive active treatment with ambrisentan.

Serum levels of alanine aminotransferase (ALT), aspartate aminotransferase (AST), alkaline phosphatase, gamma-glutamyl transpeptidase (GGT) and total bilirubin were closely monitored in all subjects throughout the study. Female subjects of childbearing potential were required to undergo monthly pregnancy tests and to use a double method of contraception to reduce risk of pregnancy during the course of the study. Male subjects were required to undergo complete semen and hormone analyses to evaluate potential effects of ambrisentan on male fertility.

After completion of the 12-week study, subjects were eligible to enroll into the long-term extension study.

Efficacy Assessments

The primary efficacy endpoint was change from baseline in 6MWD evaluated after 12 weeks of treatment compared to placebo.

The secondary efficacy endpoints included:
(a) time to clinical worsening of PAH, as defined by the time from randomization to the first occurrence of death, lung transplantation, hospitalization for PAH, atrial septostomy, study discontinuation due to addition of other PAH therapeutic agents, or study discontinuation due to 2 or more early escape criteria;
(b) change from baseline measured after 12 weeks of treatment compared to placebo in:
  (i) WHO functional class;
  (ii) SF-36® health survey physical functioning scale;
  (iii) BDI immediately following exercise; and/or
  (iv) an assessment of the safety and tolerability of the study drug; and
(c) change from baseline measured after 12 weeks of treatment compared to placebo in plasma levels of ET-1, BNP and cTnT.

Safety Assessments

All adverse effects (AEs) reported during the course of the study were reported and summaries of all AEs were prepared showing frequencies and percentages of:
(a) subjects with at least 1 AE;
(b) subjects with possibly or probably drug-related AEs;
(c) subjects with at least 1 serious AE (SAE);
(d) subjects with an AE leading to study discontinuation; and
(e) subjects who died.

Liver function test (LFT) assessments were separately summarized by severity relative to the upper limit of normal (ULN) for ALT, AST, alkaline phosphatase and total bilirubin.

For subjects who were on anticoagulants at any point during the study (regular visit or between visits), coagulation tests (PT, PTT and INR) were completed. In addition to summary statistics by study visit, changes in PT and INR were examined relative to changes in warfarin-type anticoagulant dose. These analyses focused on the values at Week 0 and Week 12 and the percentage change from Week 0 to Week 12.

The results of semen samples and their normality or abnormality were assessed by an independent male fertility expert and summarized through frequency counts and percentages by treatment. Descriptive statistics for male hormone data were prepared by treatment for the Week 0 and Week 12 visits when data were collected. Change from Week 0 to Week 12 was determined. The male fertility hormone results were analyzed in combination with the semen sample results by a second independent male fertility expert.

Frequency counts and percentages were used to summarize frequency of normal, abnormal but not clinically significant, and abnormal and clinically significant ECG results for each scheduled assessment time by treatment. All ECG data were digitally recorded and analyzed by a central reader. The following variables were analyzed: heart rate, RR and PR intervals, QRS duration, QT interval, QTcB, QTcF and ECG diagnostic variables. Descriptive statistics were used to summarize ECG results by treatment group and by week of ECG assessment.

Descriptive statistics for vital signs were reported for each scheduled assessment time by treatment and for the change from pre-dose Week 0 to each subsequent scheduled assessment by treatment.

Statistical Methods

A test of the null hypothesis of no treatment group difference in change from baseline in 6MWD with 62 subjects per group had approximately 90% power to detect an average placebo-adjusted treatment effect of 35 m based on a 2-sample t-test and a standard deviation of 55 m.

The intention-to-treat (ITT) population was defined as all randomized subjects who received at least 1 dose of study drug. For the ITT population, subjects were considered as belonging to their randomized treatment group, regardless of the actual treatment received.

The safety population was defined as all randomized subjects who received at least 1 dose of study drug. Subjects were considered as belonging to a treatment group according to the highest actual treatment dose received. Any subject who received 10 mg ambrisentan on any day was included in the 10 mg group for safety analyses in the entire study. Any subject who received 5 mg ambrisentan on any day and never received 10 mg ambrisentan on any day was included in the 5 mg group for safety analyses in the entire study. Otherwise, any subject who received only placebo was included in the placebo group for safety analyses in the study.

The primary efficacy endpoint was the change from baseline in 6MWD evaluated after 12 weeks of treatment compared to placebo, where the last observation was carried forward. Baseline 6MWD was defined as the mean 6MWD of the last two 6MWTs prior to randomization.

Change from baseline for Weeks 4, 8 and 12 in each of the two ambrisentan treatment groups were compared to placebo. The mean change was reported with 2-sided 95% confidence intervals (CIs) calculated by normal theory. The primary comparison was the change from baseline to Week 12. The Wilcoxon rank sum test stratified by idiopathic and non-idiopathic PAH subjects was used for inference. A fixed sequence approach was used to control the type I error rate accounting for the two comparisons. The higher dose was first compared to placebo. Because the p-value from the Wilcoxon rank sum test was less than 0.05 for the 5 mg ambrisentan group, the difference was considered significant, and the lower dose was compared to placebo, again at the full 0.05 α-level.

The two ambrisentan dose groups were also combined and compared to the placebo group. A p-value was reported, but for descriptive purposes only, with no impact on the fixed sequence procedure used for comparing the two individual dose groups to the placebo group.

If both ambrisentan dose groups were superior to placebo for the primary endpoint, evaluation of the secondary endpoints was done by combining the subjects from the two dose groups for comparison to the placebo group. However, if only the 10 mg group was significant for the primary endpoint, evaluation of the secondary endpoints was done only for that dose group. Secondary endpoint analyses were stratified by idiopathic and non-idiopathic PAH subjects.

The two most important secondary endpoints, time to clinical worsening of PAH and change in WHO functional class, were compared to placebo using a weighted version of Hommel's extension of the Simes test, with an overall α of 0.05. Time to clinical worsening was assigned a weight of 80% while change in WHO functional class received 20% of the weight. These two tests served as a parallel gatekeeper, allowing the physical functioning scale of the SF-36® health survey to be tested if at least one of the first two secondary endpoints was significant. Lastly, the BDI was tested conditional on a significant result from the test of the SF-36® physical functioning scale.

Additional measures of interest included change from baseline measured after 12 weeks of treatment compared to placebo in ET-1, BNP and cTnT.

Results (Example 2)

Patients (Study Population)

Disposition of randomized subjects is shown in Table 2.1.

TABLE 2.1

| Subject disposition (% of randomized subjects) | | | | |
|---|---|---|---|---|
|  | Placebo (N = 67) | 5 mg ambrisentan (N = 67) | 10 mg ambrisentan (N = 68) | Combined ambrisentan (N = 135) |
| Randomized | 67 (100.0) | 67 (100.0) | 68 (100.0) | 135 (100.0) |
| Completed | 57 (85.1) | 63 (94.0) | 63 (92.6) | 126 (93.3) |
| Withdrew | 10 (14.9) | 4 (6.0) | 5 (7.4) | 9 (6.7) |
| Reasons for withdrawal: | | | | |
| Adverse event | 1 (1.5) | 1 (1.5) | 1 (1.5) | 2 (1.5) |
| Withdrawal of consent | 1 (1.5) | 0 (0.0) | 0 (0.0) | 0 (0.0) |
| Treatment with other PAH therapeutic agents | 1 (1.5) | 0 (0.0) | 0 (0.0) | 0 (0.0) |
| Other | 1 (1.5) | 2 (3.0) | 1 (1.5) | 3 (2.1) |
| Early escape | 4 (6.0) | 0 (0.0) | 2 (2.9) | 2 (1.5) |

A total of 201 subjects, with a mean age of 50.1 years, received at least 1 dose of study drug and were included in the ITT and safety populations. A majority of the subjects enrolled were female (83.6%) and Caucasian (69.2%). More than two-thirds (68.7%) of the subjects were residents of the U.S.; the others were distributed in Central and South America (20.9%) and the rest of the world (10.4% in Australia, Austria, Hungary and Italy).

The number of years that PAH was present prior to participation in the study was calculated from the date that PAH was diagnosed until the date that informed consent was signed. For subjects who had a diagnosis of PAH confirmed at the screening visit for this study, the number of years of PAH present prior to this study was set to zero. The mean number of years that PAH was present prior to participation in this study was slightly longer for the placebo (2.14±3.63 years) than for the 5 mg (1.86±4.36 years) and 10 mg (1.40±2.39 years) groups. The median number of years that PAH was present was less than 1 year for each treatment group: placebo, 0.54 years; 5 mg, 0.33 years; 10 mg, 0.60 years.

Of the subjects enrolled, 63% had a diagnosis of idiopathic PAH prior to enrollment, and 37% had PAH associated with CTD, anorexigen use or HIV infection; idiopathic and non-idiopathic PAH subjects were equally distributed between the treatment groups. Nearly all of the subjects had either WHO functional class II (32.3%) or class III (58.2%) symptoms at baseline; only a small percentage of subjects had WHO class I (2.5%) or IV (7.0%) symptoms at baseline. The mean (±standard deviation (SD)) baseline 6MWD for all subjects was 341.0±75.80 m, and the mean baseline BDI was 3.8±2.02.

In general, demographic and baseline characteristics of the subjects participating were well balanced between the treatment groups. However, there were more class IV subjects in the 5 mg (9.0%) and 10 mg (10.4%) dose groups than in the placebo group (1.5%). There was also a difference in baseline 6MWD between WHO class I/II and WHO class III/IV subjects for both the placebo and combined ambrisentan groups: class I/II, 377.5 m and 372.0 m; and class III/IV, 320.6 m and 324.6 m, respectively.

The most frequently used concomitant medications were furosemide (47.3%), warfarin sodium (36.8%) and oxygen (26.4%). Minor differences were observed between dose groups in the use of concomitant medications.

Efficacy of Ambrisentan

Change in 6MWD from baseline to Week 12 in the ITT population is shown in Table 2.2.

TABLE 2.2

Change in 6MWD, meters

|  | Placebo | 5 mg ambrisentan | 10 mg ambrisentan | Combined ambrisentan |
|---|---|---|---|---|
| Baseline 6MWD, mean (SD) | 341.9 (73.47) | 339.6 (76.68) | 341.5 (78.28) | 340.5 (77.20) |
| Change from baseline to Week 12, mean (SD) | −7.8 (78.88) | +22.8 (82.98) | +43.6 (65.91) | +33.2 (75.37) |

The primary efficacy endpoint was statistically significant for both doses of ambrisentan compared to placebo. The placebo-adjusted improvement in mean 6MWD at Week 12 was +51.4 m (95% CI: 26.6 to 76.2; p<0.001) for the 10 mg group and +30.6 m (95% CI: 2.9 to 58.3; p=0.008) for the 5 mg group. For subjects in the placebo group, the mean 6MWD decreased from baseline (−7.8 m). For subjects receiving ambrisentan, improvement in 6MWD compared to placebo was observed as early as Week 4, and by Week 8 there was evidence of a dose response.

The secondary endpoint of time to clinical worsening of PAH demonstrated that ambrisentan (combined ambrisentan group) did not significantly delay the time to clinical worsening of PAH compared to placebo. However, twice as many subjects in the placebo group (n=6) had an event of clinical worsening compared to each of the ambrisentan dose groups (3 subjects each in the 5 mg and 10 mg dose groups). Furthermore, the hazard ratio showed a 50% reduction in the probability of clinical worsening occurring at any given time for a subject receiving ambrisentan, when compared to placebo.

Figure 2:
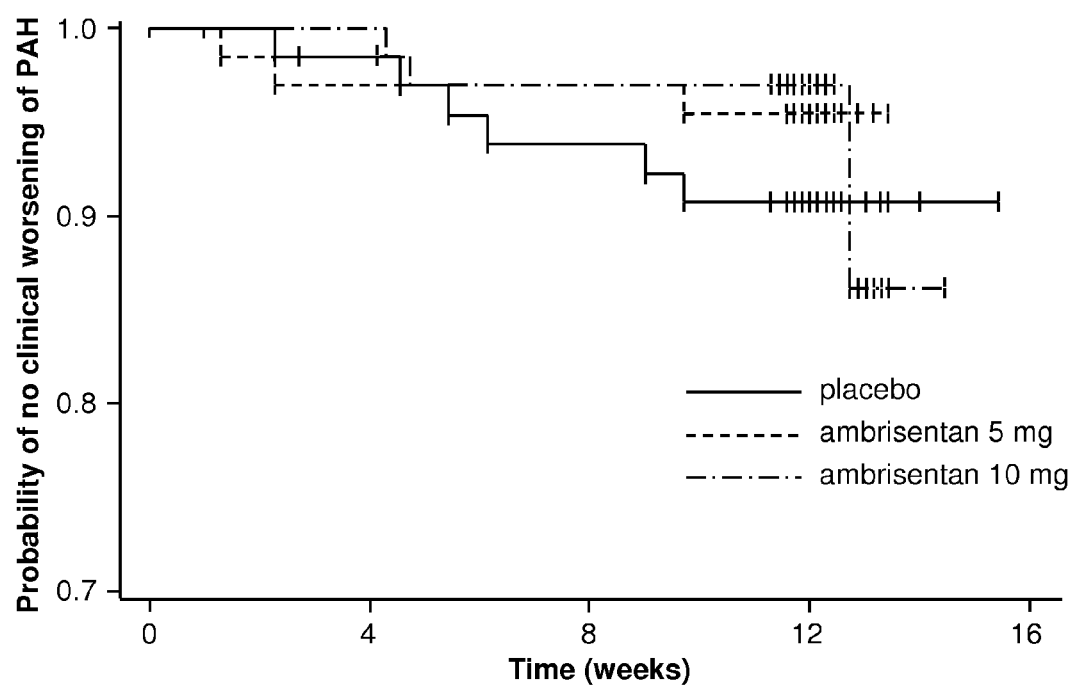
FIG. 2 provides Kaplan-Meier curves for time to clinical worsening of PAH from the study described in Example 2.

The time to clinical worsening of PAH is displayed in FIG. 2 as a Kaplan-Meier event-free curve through Week 12 for each treatment group in the ITT population. The Kaplan-Meier curve decreases sharply in the 10 mg dose group after 12 weeks due to a single event that occurred after most subjects had completed the study.

A summary of events defining clinical worsening by treatment group is presented in Table 2.3.

TABLE 2.3

Clinical worsening events (% of ITT population)

| Event | Placebo (N = 67) | 5 mg ambrisentan (N = 67) | 10 mg ambrisentan (N = 68) | Combined ambrisentan (N = 135) |
|---|---|---|---|---|
| Death | 2 (3.0) | 1 (1.5) | 1 (1.5) | 2 (1.5) |
| Lung transplantation | 0 (0.0) | 0 (0.0) | 0 (0.0) | 0 (0.0) |
| Hospitalization for PAH | 2 (3.0) | 2 (3.0) | 2 (3.0) | 4 (3.0) |
| Atrial septostomy | 0 (0.0) | 0 (0.0) | 0 (0.0) | 0 (0.0) |
| Study discontinuation due to addition of PAH treatment | 1 (1.5) | 0 (0.0) | 1 (1.5) | 1 (0.7) |
| Escape criteria | 3 (4.5) | 0 (0.0) | 2 (3.0) | 2 (1.5) |
| Total subjects with ≧1 event | 6 (9.0) | 3 (4.5) | 3 (4.5) | 6 (4.5) |

Of the 2 (3.0%) subjects in the placebo group hospitalized for PAH, 1 was hospitalized for right heart failure and 1 for right ventricular failure. Comparatively, 4 (3.0%) subjects receiving ambrisentan were hospitalized for PAH, of whom 2 (1 each in the 5 mg and 10 mg dose groups) were hospitalized for worsening right heart failure, and the other 2 for increased shortness of breath with increased peripheral edema (5 mg) and worsening PAH with severe peripheral edema (10 mg).

There were a total of 4 deaths reported during this study or within 30 days of the last dose of study drug. In the placebo group, 2 (3.0%) subjects died, and 1 (1.5%) subject each in the 5 mg and 10 mg dose groups died. All 4 deaths were captured as clinical worsening events.

Change in WHO functional class from baseline to Week 12 in the ITT population is shown in Table 2.4.

TABLE 2.4

Change in WHO functional class (% of ITT population)

| Change (no. of classes) | Placebo (N = 67) | 5 mg ambrisentan (N = 67) | 10 mg ambrisentan (N = 68) | Combined ambrisentan (N = 135) |
|---|---|---|---|---|
| −2 | 1 (1.5) | 1 (1.5) | 5 (7.5) | 6 (4.5) |
| −1 | 15 (22.4) | 18 (26.9) | 15 (22.4) | 33 (24.6) |
| no change | 40 (59.7) | 47 (70.1) | 44 (65.7) | 91 (67.9) |
| +1 | 11 (16.4) | 1 (1.5) | 3 (4.5) | 4 (3.0) |
| +2 | 0 (0.0) | 0 (0.0) | 0 (0.0) | 0 (0.0) |

The combined ambrisentan group demonstrated a clinically relevant improvement in WHO functional class at Week 12 compared to placebo (p=0.036); similar trends were observed for each ambrisentan treatment group. Due to the multiple comparisons procedure, a statistically significant improvement compared to placebo could not be stated for this secondary endpoint. However, a more than 5-fold greater percentage of subjects in the placebo group (16.4%) deteriorated by at least 1 WHO class compared to subjects in the combined ambrisentan group (3.0%). In addition, a 3-fold greater percentage of subjects in the combined ambrisentan group (4.5%) had an improvement of 2 WHO classes compared to subjects in the placebo group (1.5%).

The percentage of subjects at least maintaining their baseline WHO functional class at Week 12 was 83.6% in the placebo group, 98.5% in the 5 mg dose group and 95.5% in the 10 mg dose group.

Change in SF-36® health survey parameters from baseline to Week 12 is shown in Table 2.5.

TABLE 2.5

Change in SF-36 ® health survey parameters, mean (SD)

| Parameter | Placebo | 5 mg ambrisentan | 10 mg ambrisentan | Combined ambrisentan |
|---|---|---|---|---|
| Physical functioning | +2.31 ± 7.65 | +3.86 ± 7.14 | +4.52 ± 7.16 | +4.10 ± 8.39 |
| Role-physical | +2.81 ± 11.36 | +4.22 ± 10.52 | +6.67 ± 10.35 | +5.45 ± 10.47 |
| Bodily pain | +0.22 ± 10.70 | −1.43 ± 13.21 | +2.26 ± 12.22 | +0.42 ± 12.81 |
| General health | +1.94 ± 7.50 | +0.08 ± 8.45 | +3.25 ± 8.81 | +1.66 ± 8.74 |
| Vitality | +2.38 ± 10.06 | +2.38 ± 10.06 | +5.03 ± 10.07 | +3.71 ± 10.11 |
| Social functioning | +2.31 ± 11.60 | +1.11 ± 13.63 | +4.11 ± 11.77 | +2.61 ± 12.78 |
| Role-emotional | +2.84 ± 12.63 | +1.41 ± 13.95 | +2.98 ± 17.37 | +2.19 ± 15.71 |
| Mental health | +0.27 ± 8.09 | +0.81 ± 9.67 | +1.55 ± 12.66 | +1.18 ± 11.23 |
| Physical component summary | +1.82 ± 9.25 | +1.88 ± 8.68 | +4.79 ± 7.90 | +3.34 ± 8.40 |
| Mental component summary | +1.56 ± 9.00 | +0.50 ± 10.50 | +2.11 ± 13.17 | +1.30 ± 11.89 |

An increase in the physical function scale of the SF-36® Health Survey was observed in the combined ambrisentan group at Week 12 (4.10±8.39); however, this increase was not significantly different from placebo (2.31±7.65). For most of the SF-36® scales there was a general trend of greater increases for the 10 mg group compared to the 5 mg and placebo groups.

A clinically relevant improvement in BDI was observed at Week 12 for the combined ambrisentan group, with a placebo-adjusted BDI of −0.6 (95% CI: −1.2 to 0.0; p=0.017). Dose-dependent improvements in BDI were also observed for both the 5 mg and 10 mg dose groups compared to placebo. Due to the multiple comparisons procedure, a statistically significant improvement compared to placebo could not be stated for this secondary endpoint.

At Week 12, the geometric mean percent change in plasma ET-1 increased by 34% (95% CI: 11% to 63%) in the placebo group. The geometric mean percent change in plasma ET-1 increased from baseline by 96% (95% CI: 53% to 151%; p=0.019 versus placebo) in the 5 mg group and by 48% (95% CI: 19% to 84%; p=0.169 versus placebo) in the 10 mg group. The change from baseline was substantially greater than placebo for the 5 mg group, but not for the 10 mg group.

At baseline, approximately 90% of plasma cTnT concentrations were below the level of quantification (0.01 ng/ml). Changes in cTnT concentrations during the 12-week study were minor and not remarkably different from zero.

At Week 12, the geometric mean percent change in plasma BNP increased by 9% (95% CI: −16% to 41%) in the placebo group. In contrast, the geometric mean percent change in plasma BNP decreased from baseline by 30% (95% CI: −43% to −14%; p=0.002 versus placebo) in the 5 mg group and by 45% (95% CI: −57% to −29%; p<0.001 versus placebo) in the 10 mg group. The decrease from baseline was substantially greater than placebo for the 5 mg group and the 10 mg group.

Efficacy by Subgroup

Improvements in 6MWD were observed for both WHO functional class I/II and class III/IV subjects at Week 12, however, a slightly greater improvement was observed for class III/IV subjects. For the class I/II subgroup, the placebo-adjusted 6MWD increase from baseline at Week 12 was +25.6 m and +42.0 m for the 5 mg and 10 mg dose groups, respectively. For the class III/IV subgroup, the placebo-adjusted 6MWD increase from baseline at Week 12 was +34.1 m and +56.9 m for the 5 mg and 10 mg dose groups, respectively.

Improvements in 6MWD at Week 12 were observed in both ambrisentan dose groups for the idiopathic PAH subgroup and in the 10 mg group for the non-idiopathic PAH subgroup. There was greater improvement observed in subjects with idiopathic PAH than in subjects with non-idiopathic PAH. For the idiopathic PAH subgroup, the placebo-adjusted 6MWD increased from baseline at Week 12 by +42.9 m and +56.9 m for the 5 mg and 10 mg dose groups, respectively. For the non-idiopathic PAH subgroup, the placebo-adjusted 6MWD increase from baseline at Week 12 was +10.2 m and +43.0 m, for the 5 mg and 10 mg dose groups, respectively.

Improvements in 6MWD at Week 12 were observed in both ambrisentan dose groups for female subjects. The placebo-adjusted 6MWD increased from baseline at Week 12 by +30.9 m and +57.7 m for the 5 mg and 10 mg dose groups, respectively. For male subjects, the placebo-adjusted 6MWD increase from baseline at Week 12 was +19.9 m and +13.1 m for the 5 mg and 10 mg dose groups, respectively.

Subjects not receiving calcium channel blockers (CCBs) during the study demonstrated an improvement in 6MWD at Week 12 compared to placebo after receiving ambrisentan, with a placebo-adjusted increase from baseline of +38.7 m and +67.9 m for the 5 mg and 10 mg dose groups, respectively. Subjects receiving CCBs during the study also had an improvement in 6MWD compared to placebo after receiving ambrisentan, with a placebo-adjusted increase from baseline of +15.1 m and +19.6 m for the 5 mg and 10 mg dose groups, respectively.

Subjects not receiving supplemental oxygen demonstrated an improvement in 6MWD at Week 12 compared to placebo that was similar to the overall study population. Subjects in the placebo group who received supplemental oxygen during the study had a decrease (−25.5 m) from baseline in mean 6MWD at Week 12; whereas subjects in the 5 mg (+21.1 m) and 10 mg (+48.0 m) groups had notable increases from baseline in mean 6MWD.

Safety Results

A summary of adverse events recorded is shown in Table 2.6.

TABLE 2.6

Global summary of adverse events (% of safety population)

| Subjects | Placebo (N = 67) | 5 mg ambrisentan (N = 67) | 10 mg ambrisentan (N = 67) | Combined ambrisentan (N = 134) |
|---|---|---|---|---|
| with at least 1 AE | 56 (83.5) | 56 (83.6) | 53 (79.1) | 109 (81.3) |
| with at least 1 related AE | 21 (31.3) | 34 (50.7) | 29 (43.3) | 63 (47.0) |
| with at least 1 SAE | 7 (10.4) | 4 (6.0) | 7 (10.4) | 11 (8.2) |
| with an AE leading to study discontinuation | 4 (6.0) | 2 (3.0) | 2 (3.0) | 4 (3.0) |
| who discontinued the study via early escape | 4 (6.0) | 0 (0.0) | 2 (3.0) | 2 (1.5) |
| who died | 2 (3.0) | 1 (1.5) | 1 (1.5) | 2 (1.5) |

During this 12-week study, 83.5% of the subjects in the placebo group experienced at least 1 AE. Similarly, 83.6% of subjects in the 5 mg dose group and 79.1% of subjects in the 10 mg dose group experienced at least 1 AE during the study.

Overall, more subjects in the placebo group compared to the ambrisentan groups prematurely discontinued from the study due to death, SAEs, AEs, and/or the early escape procedure. A greater percentage of subjects in the placebo group (6.0%) met the criteria for early escape, compared to subjects in the combined ambrisentan group (1.5%).

In general, a similar percentage of AEs were assessed as severe in the placebo and 10 mg groups (19.4% and 17.9%, respectively), whereas a lower percentage of AEs were assessed as severe in the 5 mg group (6.0%). A similar percentage of AEs were assessed as moderate in the placebo and 10 mg groups (38.8% and 37.3%, respectively), whereas a higher percentage of AEs were assessed as moderate in the 5 mg group (50.7%). The most frequent AE in the combined ambrisentan group was peripheral edema, and most events were assessed as mild or moderate.

None of the 134 subjects who received ambrisentan developed any elevated serum aminotransferase concentrations >3×ULN, compared to 2 subjects in the placebo group. Further, there were no notable mean changes from baseline at Week 12 for serum ALT and AST, and no differences between treatment groups.

The changes in total bilirubin at Week 12 were shown to be substantially decreased in the 10 mg and combined ambrisentan groups, compared to placebo. The changes in alkaline phosphatase at Week 12 were shown to be substantially decreased in the 5 mg, 10 mg and combined ambrisentan groups, compared to placebo.

Mean decreases in hemoglobin concentration were observed at Week 12 for both ambrisentan dose groups compared to placebo (placebo, 0.15 g/dl; 5 mg, −0.83 g/dl; 10 mg, −0.93 g/dl). The decreases were observed early (Week 4) in the study and did not decrease further with continued treatment.

Ambrisentan had no effect on PT, INR or weekly warfarin-type anticoagulant dose.

Mean uric acid decreased slightly over the 12-week study in the placebo group (−6.5 μmol/liter); whereas a substantial decrease was observed for the 5 mg (−21.5 μmol/liter) and 10 mg (−53.3 μmol/liter) groups that appeared to be dose-dependent.

The analysis of male fertility hormones in combination with a limited number of subjects (n=12) providing serial semen samples did not suggest that ambrisentan was associated with an adverse effect on male reproductive potential.

More specifically, changes over baseline in follicle stimulating hormone (FSH) concentration at Week 12 were small, ranging from +0.52 IU/liter (placebo group) to +1.83 IU/liter (10 mg dose group). Although the FSH concentrations at Week 12 for the placebo and 5 mg dose groups (8.14±2.49 IU/liter and 9.23±7.21 IU/liter, respectively) suggest possibility of some spermatogenic dysfunction, the changes observed during the study were unlikely to be of substantial clinical relevance.

Changes in luteinizing hormone (LH) concentration at Week 12 were small: placebo, −0.07±4.72 IU/liter; 5 mg, −0.15±2.21 IU/liter; 10 mg, +1.28±10.63 IU/liter.

Changes from baseline in mean inhibin B concentration at Week 12 were similar across treatment groups: placebo, +13.2±73.55 pg/ml; 5 mg, −4.5±28.00 pg/ml; 10 mg, −7.6±50.97 pg/ml. Based on expert opinion, none of the mean inhibin B concentrations measured at baseline and Week 12 indicated presence or development of spermatogenic dysfunction.

Changes from baseline in testosterone concentration at Week 12 were −2.825±7.20 nmol/l for the placebo group, −0.099±3.48 for the 5 mg dose group, and −0.099±3.48 for the 10 mg dose group. Based on expert opinion, these data suggest that ambrisentan did not cause a negative effect on testosterone concentration in this study population.

Discussion (Example 2)

This study demonstrated that both the 5 mg and 10 mg dose of ambrisentan administered once daily provided statistically significant and clinically relevant improvements in exercise capacity and symptoms in subjects with PAH. The improvements in 6MWD were evident within 4 weeks and appeared dose-dependent by Week 8. At Week 12, the increase in 6MWD was nearly twice as large in the 10 mg dose group compared to the 5 mg dose group. Improvements in 6MWD were observed in most subgroups and, in general, appeared to be dose-dependent. Clinically relevant improvements in 6MWD were observed in subjects with WHO functional class I/II and class III/IV symptoms. Both doses also demonstrated clinically relevant treatment benefits for several secondary endpoints, including WHO functional class and BDI, as well as a notable reduction in plasma BNP.

Ambrisentan was well tolerated as indicated by the lack of dose reduction and AEs leading to premature discontinuation as well as more subjects in the placebo group discontinued due to death, SAEs, AEs, early escape, right heart failure, and/or worsening PAH. The most clinically important AEs observed in this study were peripheral edema, headache and nasal congestion. For the most part, these events were mild in severity and none led to study discontinuation. Serum aminotransferase abnormalities, which have been observed and treatment-limiting for other ERAs, were not observed in any subjects receiving ambrisentan. Furthermore, there were no increases in mean ALT and AST and there were notable decreases in mean total bilirubin and alkaline phosphatase in subjects receiving ambrisentan. Decreases in hemoglobin concentration were observed early in the study and did not decrease further with continued treatment.

In conclusion, the treatment benefits observed for the primary and secondary endpoints of this study were robust, internally consistent, and clinically relevant. Ambrisentan was well tolerated and was associated with a manageable safety profile, indicating a positive risk-to-benefit profile.

Example 3

The trials described in Examples 1 and 2 enrolled subjects from a population having PAH including idiopathic PAH and PAH associated with CTD, anorexigen use or HIV infection. Patients with pulmonary hypertension due to other etiologies were generally excluded. However, the efficacy and safety of ambrisentan observed in this classic PAH population, and the need for effective therapy in pulmonary hypertension associated with other conditions, merits evaluation in these non-traditional groups. Therefore, a further study is conducted to evaluate safety and efficacy of ambrisentan in both classic PAH patients (WHO Group 1) and in an expanded pulmonary hypertension patient population (WHO Groups 3 and 4).

This expanded population includes subjects having idiopathic and familial PAH; PAH associated with collagen vascular disease, congenital systemic-to-pulmonary shunts, HIV infection, drugs and toxins, thyroid disorders, glycogen storage disease, Gaucher disease and splenectomy; pulmonary hypertension associated with chronic obstructive pulmonary disease (COPD), interstitial lung disease (ILD), sleep-disordered breathing and alveolar hypoventilation disorders; and pulmonary hypertension due to thromboembolic obstruction of proximal and/or distal pulmonary arteries. Four groups are of particular interest in this study:
(a) PAH associated with congenital heart defects, including Eisenmenger's syndrome;
(b) PAH associated with HIV infection;
(c) pulmonary hypertension associated with ILD; and
(d) pulmonary hypertension associated with COPD.

Subjects having pulmonary hypertension associated with ILD or COPD must demonstrate a degree of pulmonary hypertension that is disproportionate to the severity of the underlying disease. Subjects with ILD must have total lung capacity ≧60% of predicted normal, mean PAP>35 mmHg, and PVR>3.5 mmHg/l/min (280 dyne·sec/cm$^5$). Subjects with COPD must have forced expiratory volume in 1 second ≧50% of predicted normal, mean PAP>35 mmHg, and PVR>3.5 mmHg/l/min (280 dyne·sec/cm$^5$).

The study is designed to evaluate improvements compared to baseline for the overall study population and for key subgroups of interest. The study also examines safety and tolerability of ambrisentan in a broad population of subjects with pulmonary hypertension.

The target population includes men and women, 18 years or older, with pulmonary hypertension as defined by the WHO clinical classification. Subjects must have a documented history of pulmonary hypertension and be able to walk at least 150-450 meters in a 6MWT.

Subjects who have discontinued bosentan or sitaxsentan therapy due to aminotransferase abnormalities or lack of efficacy are eligible for this study. Subjects currently receiving chronic prostanoid therapy and/or an oral PDE-5 inhibitor are also eligible for this study.

All subjects must have a documented mean PAP≧25 mmHg, PVR>3 mmHg/l/min, and PCWP or LVEDP<15 mmHg. Subjects with ILD or COPD must meet the additional or stricter requirements stated above.

All hemodynamic data represent resting pressures and must be assessed no more than 1 year (52 weeks) prior to the screening visit. All pulmonary function tests must be assessed no more than 3 months (12 weeks) prior to the screening visit.

Certain etiology subgroups are of particular interest. Therefore, this study enrolls a minimum of 18 subjects in the following etiology subgroups:
(a) PAH associated with congenital heart defects, including Eisenmenger's syndrome;
(b) PAH associated with HIV infection;
(c) pulmonary hypertension associated with ILD; and
(d) pulmonary hypertension associated with COPD.

This study also enrolls a minimum of 30 PAH (WHO Group 1) subjects receiving concomitant sildenafil therapy at baseline.

Enrollment continues (up to a maximum of 200 subjects) until the enrollment goals for each of the etiology subgroups, as well as the sildenafil subgroup, have been met.

The primary objective of this study is to evaluate effect of ambrisentan on exercise capacity in a broad population of subjects with pulmonary hypertension. Secondary objectives are to evaluate effects of ambrisentan on other clinical measures of pulmonary hypertension, long-term treatment success and survival. In addition, safety and tolerability of ambrisentan will be evaluated. Efficacy and safety will be evaluated in the overall study population and in various subgroups.

Anecdotal evidence suggests that patients with non-classical pulmonary hypertension may respond more slowly to therapy than the classical PAH population; therefore, the primary analysis of efficacy is evaluated after 24 weeks of treatment. Eligible subjects receive 5 mg ambrisentan once daily for the first 24 weeks. One dose reduction is permitted during the 24-week fixed-dose treatment period if a subject is not tolerating study drug (e.g., 5 mg to 2.5 mg). After the initial 24-week treatment period, investigators are allowed to adjust study drug dose as clinically indicated (available doses are 2.5 mg, 5 mg and 10 mg).

Subjects are monitored with clinical laboratory tests every 4 weeks throughout the study. These safety laboratory tests may be performed at a local phlebotomy laboratory or at the investigator clinic. In addition, the investigator assesses each subject for safety and efficacy at Week 4, Week 12 and Week 24. Following Week 24, subjects are assessed for safety and efficacy every 24 weeks.

Subjects who have received stable sildenafil treatment for at least 4 weeks are permitted to enroll in this study and continue receiving sildenafil in combination with ambrisentan. Subjects who are not receiving sildenafil treatment prior to enrollment are permitted to initiate concomitant sildenafil treatment; however, prior to addition of concomitant sildenafil treatment, investigators must conduct at least one 6MWT after the subject has received 10 mg q.d. ambrisentan for a minimum of 4 weeks. Up-titration to 10 mg q.d. ambrisentan is allowed at any time after the Week 24 visit; therefore, concomitant sildenafil treatment may be added after 28 weeks of ambrisentan monotherapy. Furthermore, addition of concomitant sildenafil treatment requires that a subject meet two or more of the following predefined criteria:
(a) a decrease from baseline of at least 20% in 6MWD;
(b) an increase of 1 or more WHO functional class; and/or
(c) worsening right ventricular failure (e.g., as indicated by increased jugular venous pressure, new or worsening hepatomegaly, ascites or peripheral edema).

The efficacy endpoints of 6MWD, WHO functional class, BDI and BNP must be assessed immediately prior to initiation of sildenafil treatment to establish baseline efficacy prior to combination therapy.

Concomitant administration of an approved prostanoid treatment (i.e., i.v. epoprostenol, i.v. or subcutaneous treprostinil, or i.v. or inhaled iloprost) is permitted at any time after the Week 12 visit. The efficacy endpoints of 6MWD, WHO functional class, BDI and BNP must be assessed immediately prior to initiation of prostanoid treatment to establish baseline efficacy prior to combination therapy.

Trough (pre-dose) and peak (2-hour) PK samples are collected at Week 0 and Week 4 to assess ambrisentan plasma concentrations. For subjects on concomitant sildenafil therapy, trough (pre-dose) and peak (1-hour) samples are collected at Week 0 and Week 4 to assess sildenafil and N-desmethylsildenafil plasma concentrations.

Male subjects complete semen and hormone analyses to evaluate potential effects of ambrisentan on male fertility.

The primary endpoint of this study is the change from baseline in 6MWD at Week 24 for all subjects.

Secondary endpoints include:
(a) clinical worsening of pulmonary hypertension, as defined by time from initiation of ambrisentan treatment to the first occurrence of death, lung transplantation, hospitalization for pulmonary hypertension, atrial septostomy, addition of chronic prostanoid treatment, or study withdrawal due to the addition of other clinically approved therapeutic agents for pulmonary hypertension;
(b) change from baseline in:
  (i) WHO functional class;
  (ii) SF-36® health survey;
  (iii) BDI immediately following exercise; and/or
  (iv) BNP;
(c) monotherapy treatment status, as defined by time from initiation of ambrisentan treatment to addition of sildenafil, iloprost, treprostinil or epoprostenol to ongoing ambrisentan treatment;
(d) failure-free treatment status, as defined by time from initiation of active treatment to the first occurrence of death, lung transplantation, or study withdrawal due to addition of other clinically approved therapeutic agents for pulmonary hypertension; and
(e) long-term survival, as defined by time from initiation of ambrisentan treatment to death.

Incidence and severity of adverse events associated with ambrisentan treatment, including elevations in AST and ALT >3xULN, are evaluated for all subjects, as well as for key etiology subgroups, and concomitant sildenafil or prostanoid treatment.

All patents and publications cited herein are incorporated by reference into this application in their entirety.

The words "comprise", "comprises", and "comprising" are to be interpreted inclusively rather than exclusively.

What is claimed is:

1. A method for treating pulmonary arterial hypertension (PAH) in a human subject, comprising administering a therapeutically effective amount of ambrisentan to the subject in combination with a therapeutically effective amount of a phosphodiesterase-5 (PDE5) inhibitor selected from sildenafil, tadalafil and vardenafil, wherein an initiation of administration of ambrisentan and the PDE5 inhibitor is not greater than about 2 years from first diagnosis of the PAH in the subject.

2. The method of claim 1, wherein the PAH is of WHO Class II, III or IV.

3. The method of claim 1, wherein the subject has idiopathic PAH.

4. The method of claim 1, wherein the subject has non-idiopathic PAH.

5. The method of claim 4, wherein the non-idiopathic PAH is secondary to scleroderma, systemic lupus erythematosus, anorexigen use or HIV infection.

6. The method of claim 1, wherein the subject has at least one of
  (a) mean PAP of at least about 25 mmHg at rest or at least about 30 mmHg while exercising,
  (b) pulmonary vascular resistance (PVR) of at least about 3 mmHg/L/min, and/or
  (c) pulmonary capillary wedge pressure (PCWP) or left ventricle end diastolic pressure (LVEDP) not greater than about 15 mmHg.

7. The method of claim 1, wherein the PDE5 inhibitor comprises tadalafil.

8. The method of claim 1, wherein the ambrisentan is administered in a daily dosage amount of about 1 mg to about 25 mg.

9. The method of claim 1, wherein the ambrisentan is administered in a daily dosage amount of about 2.5 mg to about 10 mg.

10. The method of claim 1, wherein the ambrisentan and the PDE5 inhibitor are administered in one dosage form for administration at the same time.

11. The method of claim 1, wherein the ambrisentan and the PDE5 inhibitor are administered separately at different times.

* * * * *